United States Patent
Toma et al.

(10) Patent No.: US 9,357,981 B2
(45) Date of Patent: Jun. 7, 2016

(54) ULTRASOUND DIAGNOSTIC DEVICE FOR EXTRACTING ORGAN CONTOUR IN TARGET ULTRASOUND IMAGE BASED ON MANUALLY CORRECTED CONTOUR IMAGE IN MANUAL CORRECTION TARGET ULTRASOUND IMAGE, AND METHOD FOR SAME

(71) Applicant: KONICA MINOLTA, INC., Chiyoda-ku, Tokyo (JP)

(72) Inventors: Tadamasa Toma, Kadoma (JP); Jun Ohmiya, Kyotanabe (JP); Bumpei Toji, Hashima (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 14/366,257

(22) PCT Filed: Dec. 20, 2012

(86) PCT No.: PCT/JP2012/008146
§ 371 (c)(1),
(2) Date: Jun. 17, 2014

(87) PCT Pub. No.: WO2013/094205
PCT Pub. Date: Jun. 27, 2013

(65) Prior Publication Data
US 2014/0334706 A1    Nov. 13, 2014

(30) Foreign Application Priority Data
Dec. 21, 2011  (JP) ................................. 2011-279425

(51) Int. Cl.
*G06K 9/00* (2006.01)
*A61B 8/08* (2006.01)
(Continued)

(52) U.S. Cl.
CPC ............. *A61B 8/5223* (2013.01); *A61B 8/0858* (2013.01); *A61B 8/0883* (2013.01);
(Continued)

(58) Field of Classification Search
None
See application file for complete search history.

(56) References Cited

U.S. PATENT DOCUMENTS 6,450,959 B1 * 9/2002 Mo ...................... G01S 7/52074
                                                            128/916
8,900,149 B2 * 12/2014 He ....................... A61B 8/0883
                                                            600/453
(Continued)

FOREIGN PATENT DOCUMENTS

JP       07178090 A     7/1995
JP       11164834 A     6/1999
(Continued)

OTHER PUBLICATIONS

International Search Report (ISR) dated Jan. 22, 2013 issued in International Application No. PCT/JP2012/008146.
(Continued)

*Primary Examiner* — Tahmina Ansari
(74) *Attorney, Agent, or Firm* — Holtz, Holtz & Volek PC

(57) ABSTRACT

An ultrasound diagnostic device includes: a contour extraction unit extracting a first contour image from ultrasound images obtained from spatially-successive examination positions and each including an image of an organ, a contour image indicating a contour of the organ and extracted from the organ image; a specification unit receiving, from a user, specification information specifying a manual correction target ultrasound image and correction information indicating details of a manual correction performed with respect to a first contour image extracted from the manual correction target ultrasound image; and a contour correction unit correcting the first contour image extracted from the manual correction target ultrasound image according to the correction information. The contour extraction unit further extracts a second contour image from a target ultrasound image by using information indicating the corrected first contour image. The target ultrasound image differs from the manual correction target image.

14 Claims, 27 Drawing Sheets

(51) Int. Cl.
*A61B 8/13* (2006.01)
*A61B 8/00* (2006.01)

(52) U.S. Cl.
CPC ............... *A61B8/0891* (2013.01); *A61B 8/13* (2013.01); *A61B 8/463* (2013.01); *A61B 8/466* (2013.01); *A61B 8/469* (2013.01); *A61B 8/483* (2013.01); *A61B 8/467* (2013.01)

(56) References Cited

U.S. PATENT DOCUMENTS

| | | | | |
|---|---|---|---|---|
| 9,072,489 | B2* | 7/2015 | Chono | A61B 8/461 |
| 2002/0102023 | A1 | 8/2002 | Yamauchi | |
| 2005/0228276 | A1* | 10/2005 | He | A61B 8/0883 600/437 |
| 2008/0114244 | A1* | 5/2008 | Murashita | A61B 8/14 600/443 |
| 2008/0159610 | A1 | 7/2008 | Haas et al. | |
| 2014/0018680 | A1* | 1/2014 | Guracar | A61B 8/463 600/440 |
| 2014/0303499 | A1* | 10/2014 | Toma | A61B 8/06 600/454 |
| 2014/0334706 | A1* | 11/2014 | Toma | A61B 8/0883 382/131 |

FOREIGN PATENT DOCUMENTS

| | | | |
|---|---|---|---|
| JP | 2000296129 A | | 10/2000 |
| JP | 2002224116 A | | 8/2002 |
| JP | 2008142519 A | | 6/2008 |
| JP | 2008161688 A | | 7/2008 |
| JP | WO2011/083789 | * | 7/2011 |

OTHER PUBLICATIONS

Chinese Office Action (and English translation thereof) dated Aug. 12, 2015, issued in counterpart Chinese Application No. 201280063696.1.

* cited by examiner

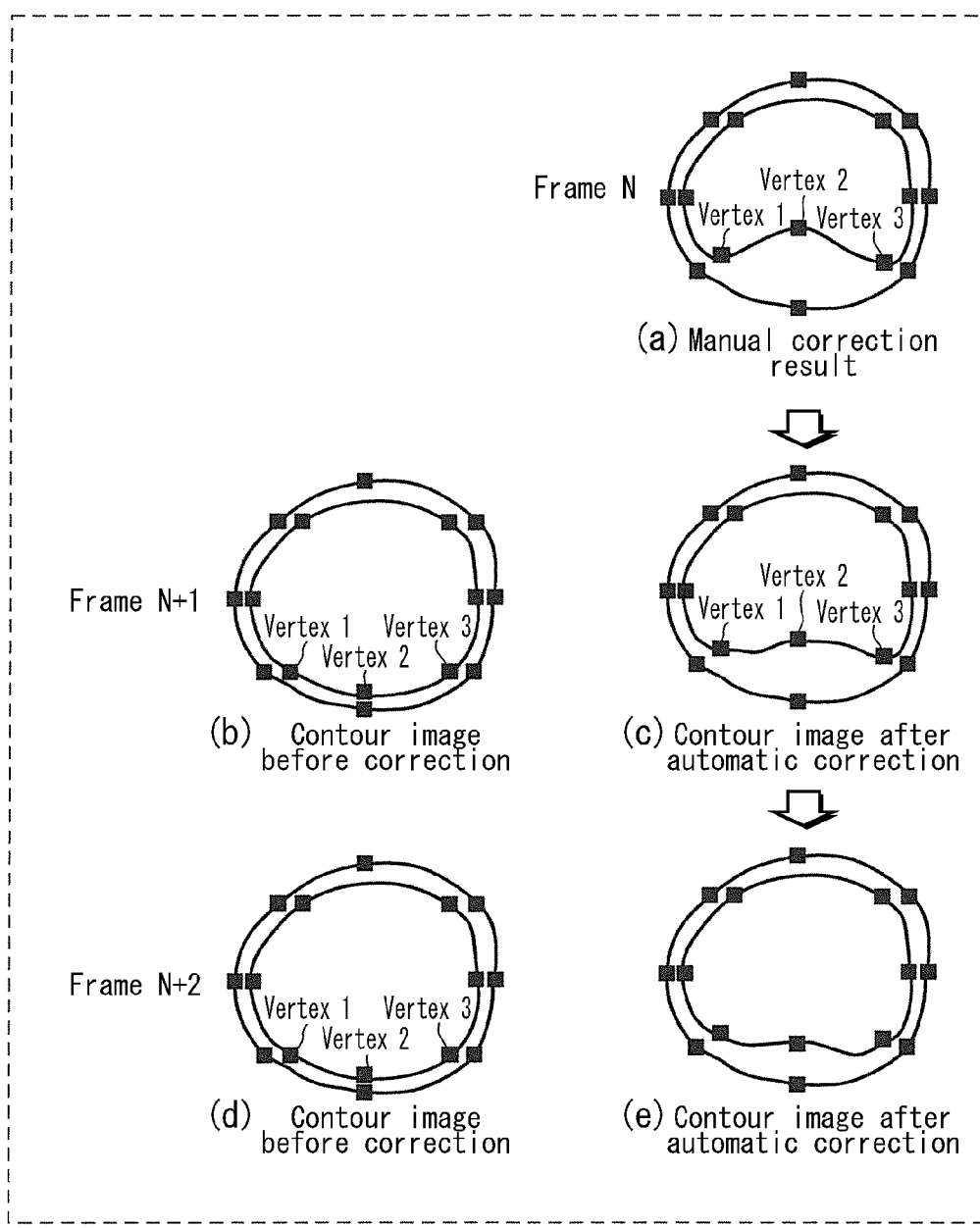

ULTRASOUND DIAGNOSTIC DEVICE FOR EXTRACTING ORGAN CONTOUR IN TARGET ULTRASOUND IMAGE BASED ON MANUALLY CORRECTED CONTOUR IMAGE IN MANUAL CORRECTION TARGET ULTRASOUND IMAGE, AND METHOD FOR SAME

TECHNICAL FIELD

The present disclosure relates to an ultrasound diagnostic device and a contour extraction method.

BACKGROUND ART

There exists conventional technology disclosing a technology of extracting a contour of a blood vessel from diagnostic images of an examination subject and allowing a user to correct the contour so extracted (Patent Literature 1).

CITATION LIST

Patent Literature

[Patent Literature 1]
Japanese Patent Application Publication No. 2008-161688

SUMMARY OF INVENTION

Technical Problem

However, according to this conventional technology, a user needs to manually perform contour correction with respect to each and every diagnostic image requiring correction of the contour of the blood vessel therein. Due to this, a great amount of time is required to perform correction.

In view of the above, one aspect of the present disclosure is an ultrasound diagnostic device that more accurately extracts images of a contour (contour images) of an organ from a plurality of diagnostic images in a short amount of time.

Solution to Problem

One aspect of the present disclosure is an ultrasound diagnostic device including: a contour extraction unit configured to extract a first contour image from each of a plurality of ultrasound images obtained from spatially-successive examination positions and each including an image of an organ, a contour image extracted from an ultrasound image being an image indicating a contour of the organ and being extracted from an image of the organ appearing in the ultrasound image; a specification unit configured to receive, from a user of the ultrasound diagnostic device, specification information specifying a manual correction target ultrasound image among the ultrasound images and correction information indicating details of a manual correction that the user performs with respect to a first contour image extracted from the manual correction target ultrasound image; and a contour correction unit configured to correct the first contour image extracted from the manual correction target ultrasound image according to the correction information to obtain a corrected first contour image. In the ultrasound diagnostic device, the contour extraction unit is further configured to extract a second contour image from a target ultrasound image among the ultrasound images by using information indicating the corrected first contour image, the target ultrasound image differing from the manual correction target image.

Various aspects as described above, which include both those that are general and those that are specific, may be implemented as a system, a method, an integrated circuit, a computer program, or a computer-readable recording medium such a CD-ROM, or may be implemented as a combination of any of a system, a method, a integrated circuit, a computer program, and a computer-readable recording medium.

Advantageous Effects of Invention

The ultrasound diagnostic device pertaining to one aspect of the present disclosure more accurately extracts contour images of an organ from a plurality of diagnostic images in a short amount of time.

BRIEF DESCRIPTION OF DRAWINGS

FIG. 7B is a second explanatory diagram illustrating the example of the automatic correction processing of the tunica intima.

DESCRIPTION OF EMBODIMENTS (Finding Serving as Basis of Aspects of Present Disclosure)

The present inventors have found that the following problems are observed in relation with the conventional method of extracting contour images from ultrasound images that is described in the "Background Art" section of the present disclosure.

Diagnostic imaging devices commonly used for examining living organisms include X-ray diagnostic devices, MRI (Magnetic Resonance Imaging) diagnostic devices, and ultrasound diagnostic devices. Among the above devices, ultrasound diagnostic devices in particular are advantageous for non-invasiveness and for enabling real-time usage, and therefore are widely used for medical examinations, which in the present disclosure includes health checks. An ultrasound diagnostic device is used to examine various parts of the human body, such as the heart, blood vessels, the liver, and breasts. In particular, examination of the carotid artery for determining risk of arteriosclerosis is attracting much attention in recent years.

Figure 20:
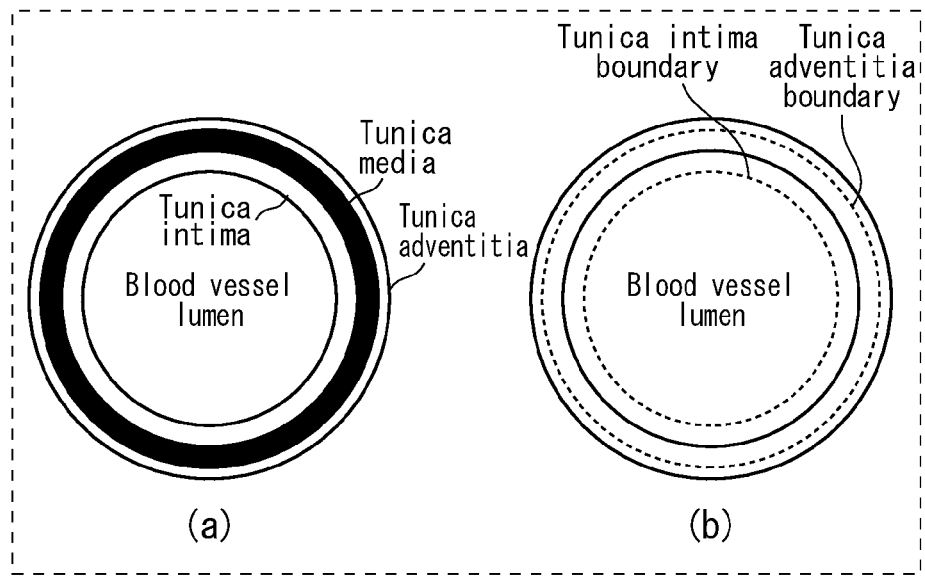
FIG. 20 are diagrams for explaining the structure of a blood vessel wall of an artery.

Portion (a) of FIG. 20 illustrates the structure of a blood vessel wall of an artery. A blood vessel wall is composed of three layers, the tunica intima, the tunica media, and the tunica adventitia. As arteriosclerosis progresses, thickness of mainly the tunica intima and the tunica media increases. In ultrasound examination of the carotid artery, an ultrasound diagnostic device is used to detect a tunica intima boundary and a tunica adventitia boundary, which are illustrated in portion (b) of FIG. 20. Thus, measurement is performed of a thickness of a combination of the tunica intima and the tunica media (the "intima-media"). A portion of the intima-media that has a thickness exceeding a predetermined value is referred to as a plaque. When a plaque is formed, depending on the size thereof, it may become necessary to remove the plaque through medicinal treatment or to remove the plaque through surgical treatment. Due to this, it is important for the measurement of the thickness of the intima-media to be performed accurately.

In the following, explanation is provided of a plaque, with reference to FIGS. 21 and 22.

Figure 21:
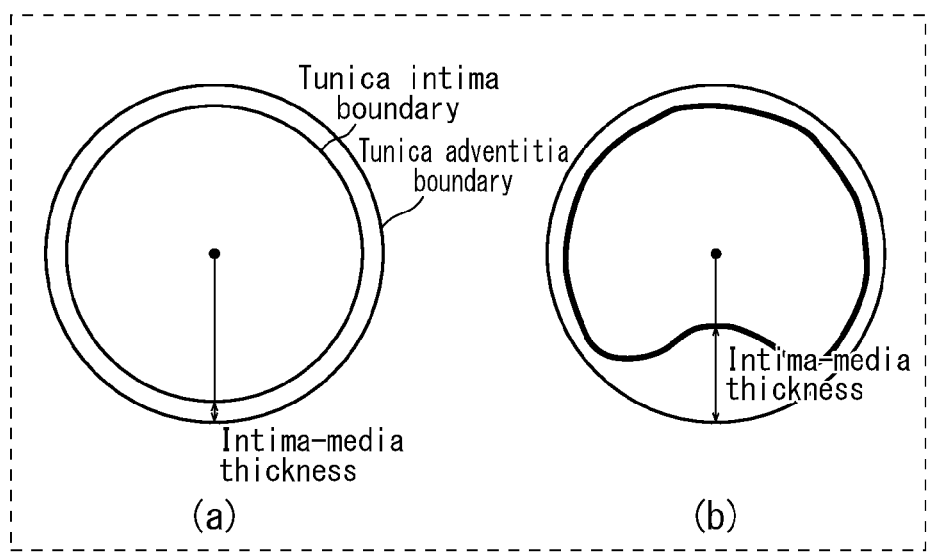
FIG. 21 are diagrams for explaining thickening of an intima-media caused by a plaque.

Portion (a) of FIG. 21 illustrates an example of the intima-media in a normal state, which is a state where thickening of the intima-media has not taken place. Portion (b) of FIG. 21 illustrates an example of the intima-media in a state where a plaque has been formed due to the progress of thickening of the intima-media. When performing examination to detect a plaque in the intima-media or the increase in thickness of the intima-media, which may later result in a plaque being formed, a user of an ultrasound diagnostic device (a person carrying out examination) measures the thickness of the intima-media while moving an ultrasound probe of the ultrasound diagnostic device over and thus scanning a wide area of the carotid artery.

Figure 22:
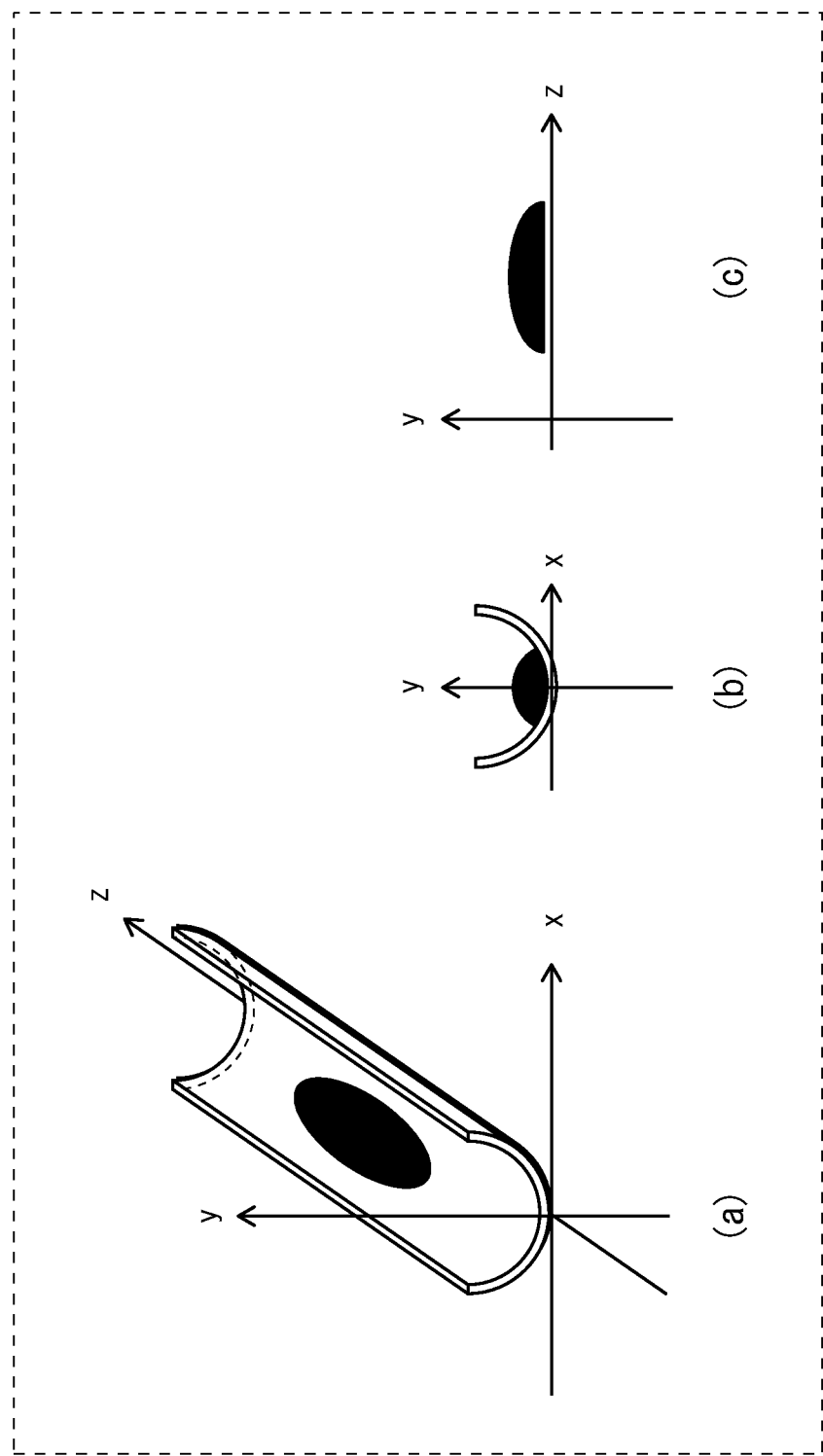
FIG. 22 is an explanatory diagram illustrating a 3D shape of a plaque.

FIG. 22 includes explanatory diagrams illustrating a three-dimensional shape of a plaque. Note that in the following, the expressions "three-dimensional" and "two-dimensional" are indicated simply as "3D" and "2D", respectively. In portion (a) of FIG. 22, a blood vessel running in a Z axis direction is illustrated in a state of being cut in half by using an imaginary plane parallel with the Z axis. In addition, in portion (a) of FIG. 22, a part of the blood vessel where a plaque exists is shown in black. Portion (b) of FIG. 22 illustrates a short-axis cross-section of the plaque (i.e., a cross-section taken along a plane perpendicular to the Z axis). FIG. 22C shows a long-axis cross-section of the plaque (i.e., a cross-section taken along a plane parallel with the Z axis).

Figure 23:
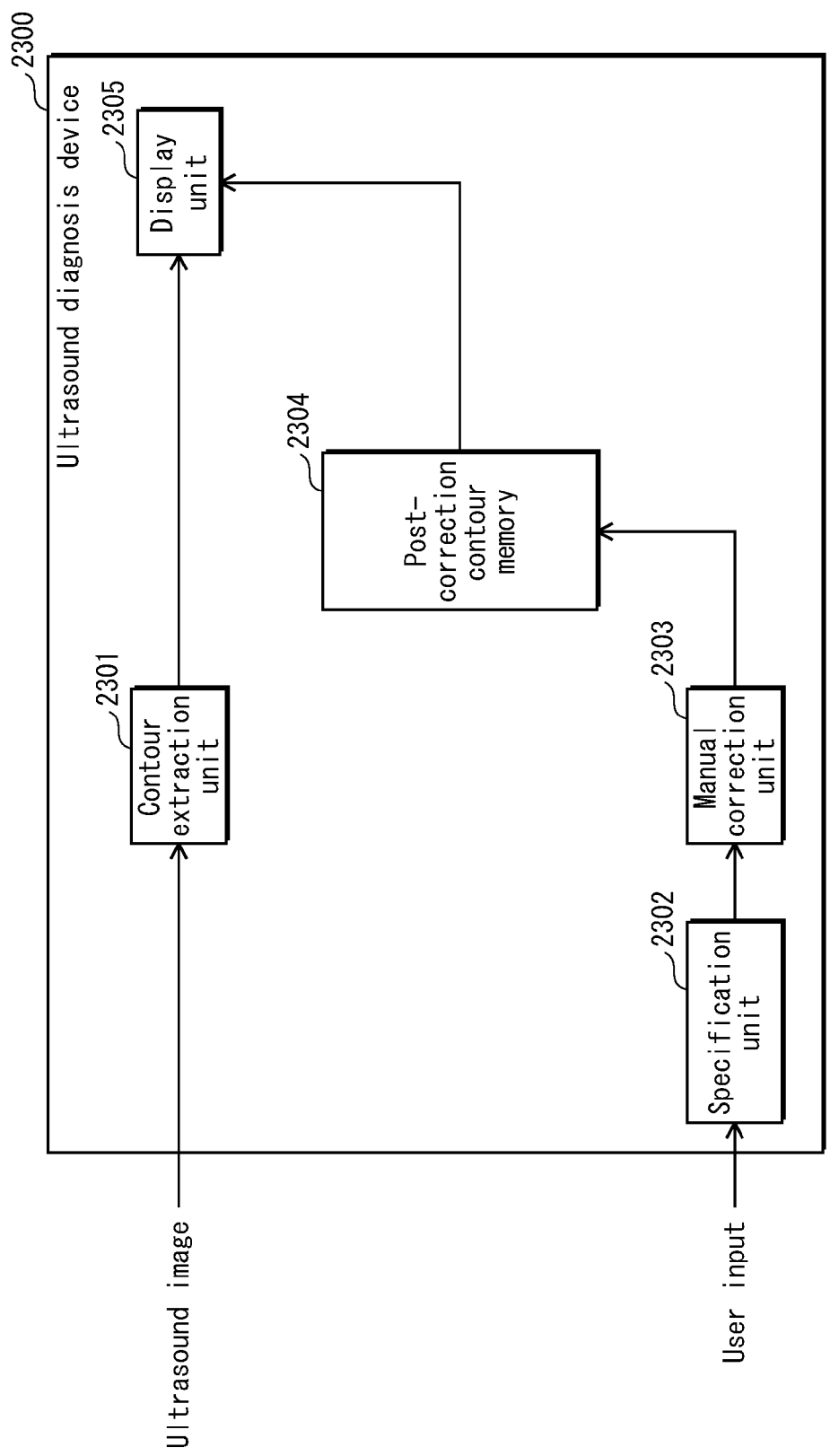
FIG. 23 is a block diagram illustrating the structure of an ultrasound diagnostic device pertaining to a technology envisaged by the present inventors.

FIG. 23 is a block diagram illustrating the structure of an ultrasound diagnostic device pertaining to a technology envisaged by the present inventors.

More specifically, FIG. 23 is a block diagram illustrating an ultrasound diagnostic device for measuring the thickness of the intima-media of the carotid artery. As illustrated in FIG. 23, an ultrasound diagnostic device 2300 includes: a contour extraction unit 2301; a specification unit 2302; a manual correction unit 2303; a post-correction contour memory 2304; and a display unit 2305.

The ultrasound diagnostic device 2300 has a function of automatically extracting contour images of a blood vessel from a plurality of ultrasound images that are obtained by scanning the blood vessel by using an ultrasound probe. In addition, the ultrasound diagnostic device 2300 also has a function allowing a user of the ultrasound diagnostic device 2300 to manually correct the blood vessel contour images that have been automatically extracted.

The contour extraction unit 2301 extracts contour images of a blood vessel from a plurality of ultrasound images that are obtained from spatially-successive examination positions. Further, the contour extraction unit 2301 inputs the blood vessel contour images so extracted to the display unit 2305.

The display unit 2305 displays the blood vessel contour image having been automatically extracted so as to be overlaid on the ultrasound images. The user, by referring to what is output by the display unit 2305, checks whether or not one or more of the blood vessel contour images having been automatically extracted need to be corrected. When judging that a given one of the blood vessel contour images needs to be corrected, the user specifies a corresponding one of the ultrasound images with respect to which correction is to be performed by using the specification unit 2302. As described in the following, the manual correction unit 2303 performs correction of the blood vessel contour image in the ultrasound image that the user specifies by using the specification unit 2303. After the correction, the display unit 2305 displays the corrected blood vessel contour image.

The manual correction unit 2303 corrects the blood vessel contour image included in the ultrasound image specified by the specification unit 2302 according to user input, and stores the result of the correction to the post-correction contour memory 2304.

Figure 24:
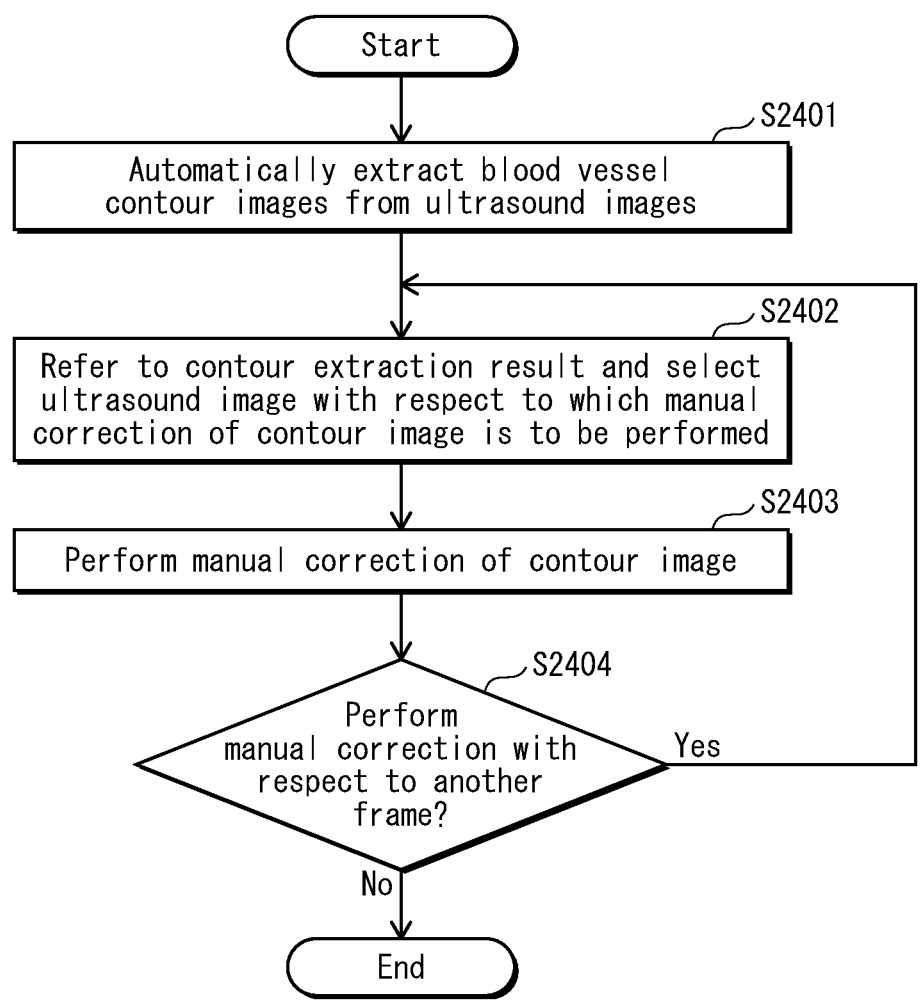
FIG. 24 is a flowchart illustrating the operations of the ultrasound diagnostic device pertaining to the technology envisaged by the present inventors.

FIG. 24 is a flowchart illustrating the operations of the ultrasound diagnostic device 2300.

In Step S2401, the contour extraction unit 2301 automatically extracts blood vessel contour images from ultrasound images.

In Step S2402, the specification unit 2302 selects an ultrasound image including a blood vessel contour image that is to be manually corrected. This selection is made according to a result of the user referring to the blood vessel contour images having been automatically extracted.

In Step S2403, the manual correction unit 2303 corrects the blood vessel contour image included in the ultrasound image selected by the specification unit 2302 according to user input. Following this point, the processing in Steps S2302 and S2303 is repeated until correction has been performed with respect to all of the ultrasound images that require manual correction.

Here, it should be noted that the ultrasound diagnostic device 2300 needs to perform manual correction (contour correction according to user input) with respect to each and every ultrasound image that requires contour correction. (Note that in the following, an ultrasound image is also referred to as a "frame".) Here, it should be noted that in many cases, a contour of a blood vessel changes continuously between frames obtained from spatially-adjacent examination positions. Due to this, when performing automatic extraction of blood vessel contour images as described above, if the extraction of a blood vessel contour image from a given frame fails, it is quite likely that the extraction of blood vessel contour images from frames close to the given frame, which are obtained from examination positions close to the examination position from which the given frame is obtained, also fails. When such a situation occurs, manual correction needs to be performed with respect to many frames, and thus, a great amount of time is required for the correction to be completed. Note that in the present disclosure, the relationship between frames (ultrasound images) may be indicated by referring to the positional relationship between the examination positions from which the frames (ultrasound images) are obtained. For example, frames obtained from spatially-adjacent examination positions may be referred to as adjacent frames, and frames obtained from examination positions close to one another may be referred to as neighboring frames.

Figure 25:
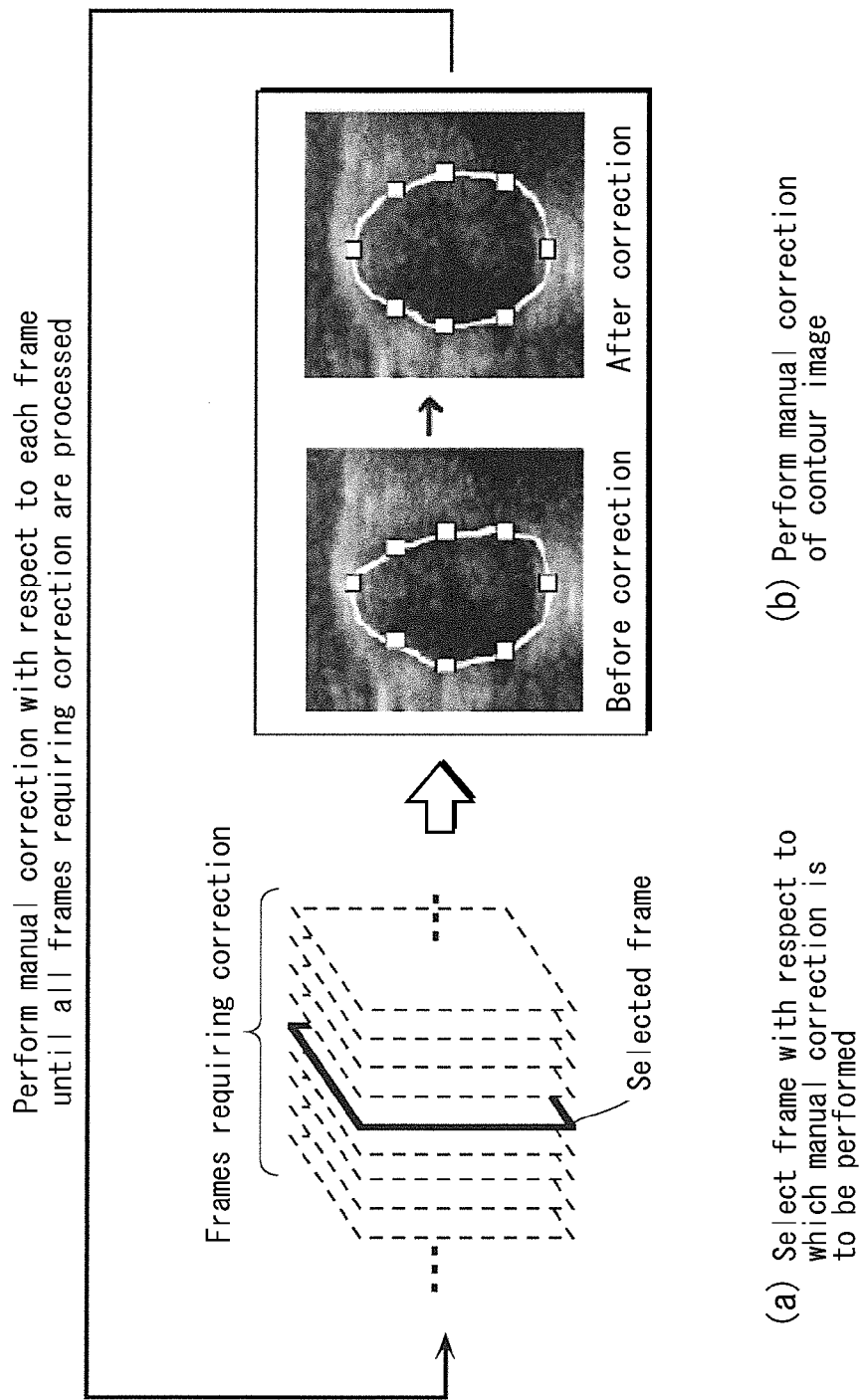
FIG. 25 is a diagram for explaining a problem with the ultrasound diagnostic device pertaining to the technology envisaged by the present inventors.

FIG. 25 is an explanatory diagram illustrating a problem with the ultrasound diagnostic device 2300. Portion (a) of FIG. 25 shows a group of frames determined as requiring contour correction. More specifically, portion (a) of FIG. 25 illustrates an example where a plurality of spatially-successive frames are selected. In the example illustrated in portion (a) of FIG. 25, the user, who may be a medical practitioner or an engineer performing examination, needs to perform manual correction processing, illustration of which is provided in portion (b) of FIG. 25, with respect to each and every one of the selected frames. Thus, the amount of labor on the side of the user is great, which is one problem with the ultrasound diagnostic device 2300.

In view of the above, the present disclosure provides, as one aspect thereof, an ultrasound diagnostic device that accurately extracts contour images of an organ from a plurality of diagnostic images in a relatively short amount of time.

One aspect of the present disclosure is an ultrasound diagnostic device including: a contour extraction unit configured to extract a first contour image from each of a plurality of ultrasound images obtained from spatially-successive examination positions and each including an image of an organ, a contour image extracted from an ultrasound image being an image indicating a contour of the organ and being extracted from an image of the organ appearing in the ultrasound image; a specification unit configured to receive, from a user of the ultrasound diagnostic device, specification information specifying a manual correction target ultrasound image among the ultrasound images and correction information indicating details of a manual correction that the user performs with respect to a first contour image extracted from the manual correction target ultrasound image; and a contour correction unit configured to correct the first contour image extracted from the manual correction target ultrasound image according to the correction information to obtain a corrected first contour image. In the ultrasound diagnostic device, the contour extraction unit is further configured to extract a second contour image from a target ultrasound image among the ultrasound images by using information indicating the corrected first contour image, the target ultrasound image differing from the manual correction target image.

According to the ultrasound diagnostic device pertaining to one aspect of the present disclosure, when correction based on user specification (manual correction) is performed with respect to a first contour image of an organ extracted from a manual correction target ultrasound image among a plurality of ultrasound images, extraction of a second contour image from an ultrasound image other than the manual correction target ultrasound image is performed according to the result of the manual correction. Thus, the ultrasound diagnostic device pertaining to one aspect of the present disclosure extracts a second contour image from an ultrasound image other than the manual correction target ultrasound image while applying the result of the manual correction performed by the user. That is, compared to conventional technology that requires users to perform manual correction with respect to each of a plurality of ultrasound images and thus necessitates a great amount of labor and time, the ultrasound diagnostic device pertaining to one aspect of the present disclosure reduces the amount of labor and time required for correcting ultrasound images. Thus, the ultrasound diagnostic device pertaining to one aspect of the present disclosure more accurately extracts contour images of an organ from a plurality of diagnostic images in a relatively short amount of time.

In the ultrasound diagnostic device pertaining to one aspect of the present disclosure, the contour extraction unit may extract the second contour image from the target ultrasound image by performing a search with respect to the target ultrasound image among the ultrasound images by using the information indicating the corrected first contour image as an initial contour image.

According to this, the ultrasound diagnostic device pertaining to one aspect of the present disclosure uses a corrected first contour image, obtained as a result of a user performing manual correction, as an initial contour image when extracting a second contour image from an ultrasound image other than a manual correction target ultrasound image. Thus, the ultrasound diagnostic device pertaining to one aspect of the present disclosure extracts contour images that are even more accurate.

In the ultrasound diagnostic device pertaining to one aspect of the present disclosure, the manual correction target ultrasound image and the target ultrasound image may be obtained from adjacent examination positions.

According to this, the ultrasound diagnostic device pertaining to one aspect of the present disclosure extracts, while applying a result of manual correction, a second contour image from an ultrasound image that is obtained from an examination position close to an examination position from which a manual correction target ultrasound image is obtained. A contour image included in an ultrasound image that is obtained from an examination position close to an examination position from which a manual correction target ultrasound image is obtained is likely to have a shape similar to that of a contour image included in the manual correction target ultrasound image. Thus, the ultrasound diagnostic device pertaining to one aspect of the present disclosure extracts contour images that are even more accurate.

In other words, in correcting contour images that are automatically extracted from a plurality of ultrasound images, the ultrasound diagnostic device pertaining to one aspect of the present disclosure, when a contour image in one frame is corrected, performs correction of an adjacent frame by automatically extracting a contour image from the adjacent frame. Thus, the ultrasound diagnostic device pertaining to one aspect of the present disclosure achieves a great reduction in time required for correction. Thus, the ultrasound diagnostic device pertaining to one aspect of the present disclosure more accurately extracts contour images of an organ from a plurality of diagnostic images in a relatively short amount of time.

In the ultrasound diagnostic device pertaining to one aspect of the present disclosure, the contour extraction unit may extract the contour image obtained as the result of performing the search with respect to the target ultrasound image as the second contour image only when the contour image obtained as the result of performing the search with respect to the target ultrasound image and a first contour image extracted from the target ultrasound image differ in shape by at least a predetermined level.

According to this, the ultrasound diagnostic device pertaining to one aspect of the present disclosure, when extracting a second contour image from a target ultrasound image by applying the result of manual correction, uses the second contour image as the result of the extraction when the second contour image and a first contour image initially extracted from the target ultrasound image differ in shape by at least the predetermined level. Meanwhile, the ultrasound diagnostic device pertaining to one aspect of the present disclosure, when the second contour image and the first contour image extracted from the target ultrasound image do not differ in shape by at least the predetermined level, uses the first contour image extracted from the target ultrasound image as the result of the extraction. Thus, the ultrasound diagnostic device pertaining to one aspect of the present disclosure uses the second contour image as the result of the extraction only when the difference between the second contour image and the first organ contour image is great.

In the ultrasound diagnostic device pertaining to one aspect of the present disclosure, the contour extraction unit may be further configured to (i) perform the search with respect to another target ultrasound image among the ultrasound images by using information indicating the second contour image extracted from the target ultrasound image as an initial contour image, and (ii) extract, from the other target ultrasound image, a contour image obtained as a result of performing the search with respect to the other target ultrasound image as a second contour image extracted from the other ultrasound image, the other target ultrasound image differing from the manual correction target ultrasound image and the target ultrasound image.

According to this, the ultrasound diagnostic device pertaining to one aspect of the present disclosure extracts a second contour image from another target ultrasound image while applying the result of correction performed with respect to the target ultrasound image. The target ultrasound image is corrected while applying the result of manual correction. Thus, the ultrasound diagnostic device pertaining to one aspect of the present disclosure more accurately extracts contour images of an organ from a plurality of diagnostic images in a relatively short amount of time.

In the ultrasound diagnostic device pertaining to one aspect of the present disclosure, the target ultrasound image and the other target ultrasound image may be obtained from adjacent examination positions.

According to this, the ultrasound diagnostic device pertaining to one aspect of the present disclosure extracts a second contour image from another target ultrasound image while applying the result of correction performed with respect to the target ultrasound image. The other target ultrasound image is obtained from an examination position close to an examination position from which the target ultrasound image is obtained.

In the ultrasound diagnostic device pertaining to one aspect of the present disclosure, the contour extraction unit may perform multiple iterations of the search, each time processing a different one of the plurality of ultrasound images, the contour extraction unit performing the search starting from the target ultrasound image, which is closest in terms of examination position to the manual correction target ultrasound image, and subsequently processing, one by one, other ones of the ultrasound images in order of closeness, in terms of examination position, to the manual correction target ultrasound image, and when performing a given iteration of the search, the contour extraction unit may use a contour image obtained as a result of performing a previous iteration of the search as an initial contour image.

Further, in the ultrasound diagnostic device pertaining to one aspect of the present disclosure, the contour extraction unit may perform multiple iterations of the search while a contour image obtained as a result of performing a present iteration of the search and a first contour image extracted from one of the ultrasound images processed in the present iteration of the search differ in shape by at least the predetermined level.

According to this, the ultrasound diagnostic device pertaining to one aspect of the present disclosure extracts a contour image from each of a plurality of ultrasound images, one image at a time in order of closeness, in terms of examination position, to a manual correction target ultrasound image, and in each iteration of the extraction, uses the result of the extraction performed in a previous iteration of the search for extracting a contour image in a present iteration.

In the ultrasound diagnostic device pertaining to one aspect of the present disclosure, the organ may be a blood vessel, and a contour image extracted by the contour extraction unit from an ultrasound image may indicate a contour of a layer of the blood vessel.

Further, in the ultrasound diagnostic device pertaining to one aspect of the present disclosure, the organ may be a blood vessel, and a contour image extracted by the contour extraction unit from an ultrasound image may indicate a contour of a tunica intima or a tunica adventitia of the blood vessel.

According to this, the ultrasound diagnostic device pertaining to one aspect of the present disclosure corrects a contour image of a blood vessel, or corrects a contour image of the tunica intima or the tunica adventitia.

Further, in the ultrasound diagnostic device pertaining to one aspect of the present disclosure, the contour extraction unit may perform multiple iterations of the search, each time processing a different one of the plurality of ultrasound images, the contour extraction unit performing the search starting from the target ultrasound image, which is closest in terms of examination position to the manual correction target ultrasound image, and subsequently processing, one by one, other ones of the ultrasound images in order of closeness, in terms of examination position, to the manual correction target ultrasound image, and the contour extraction unit may perform multiple iterations of the search while a distance between contour images of the tunica intima and the tunica adventitia, obtained as a result of performing a present iteration of the search, exceeds a predetermined threshold value.

According to this, the ultrasound diagnostic device pertaining to one aspect of the present disclosure extracts a second contour image from each ultrasound image in which a thickness of a blood vessel layer obtained as a result of the extraction is greater than or equal to the predetermined threshold value. That is, the ultrasound diagnostic device pertaining to one aspect of the present disclosure performs the extraction of a second contour image only with respect to a plaque portion of the blood vessel.

The ultrasound diagnostic device pertaining to one aspect of the present disclosure may further include: a three-dimensional image generation unit that generates a three-dimensional image of the organ by combining contour images of the organ extracted from the ultrasound images by the contour extraction unit according to respective examination positions from which the ultrasound images are obtained.

According to this, the ultrasound diagnostic device pertaining to one aspect of the present disclosure generates a three-dimensional image of a blood vessel by combining corrected blood vessel contour images. Thus, a three-dimensional shape of a blood vessel is presented to a user of the ultrasound diagnostic device, whereby the user is able to intuitively recognize a contour of the organ.

In the ultrasound diagnostic device pertaining to one aspect of the present disclosure, the specification unit may receive, from the user as the correction information, additional contour information indicating a contour image corresponding to another image of the organ appearing in the manual correction target ultrasound image, and the contour correction unit may correct the manual correction target ultrasound image by creating the contour image corresponding to the other image of the organ in the manual correction target ultrasound image.

According to this, even when there exists a contour of a blood vessel that the ultrasound diagnostic device is not capable of initially extracting, a blood vessel contour image is newly created according to user specification.

In the ultrasound diagnostic device pertaining to one aspect of the present disclosure, the contour extraction unit may be further configured to, when two or more contour images overlap one another in the manual correction target ultrasound image after the correction by the contour correction unit, merge the two or more overlapping contour images into a single contour image, and extract the single contour image from the manual correction target ultrasound image.

According to this, when a blood vessel contour image newly created according to user specification overlaps with another blood vessel contour image, the ultrasound diagnostic device forms a blood vessel contour image by treating the two blood vessel contour images as a single blood vessel contour image.

In the ultrasound diagnostic device, when (i) the specification information received by the specification unit specifies, from among the ultrasound images, each of a first ultrasound image including one image of the organ and a second ultrasound image including two images of the organ as the manual correction target ultrasound image, and (ii) the correction information received by the specification unit is additional contour information indicating one contour image corresponding to the one image of the organ in the first ultrasound image and two contour images corresponding to the two images of the organ in the second ultrasound image, the contour correction unit may correct the first ultrasound image by creating the one contour image according to the correction information and correct the second ultrasound image by creating the two contour images according to the correction information.

According to this, the ultrasound diagnostic device pertaining to one aspect of the present disclosure, when there exists a contour of a Y-shaped blood vessel that is not initially extracted, newly creates a contour image of the Y-shaped blood vessel according to user specification.

Another aspect of the present disclosure is a contour extraction method for an ultrasound diagnostic device, the contour extraction method including: extracting a first contour image from each of a plurality of ultrasound images obtained from spatially-successive examination positions and each including an image of an organ, a contour image extracted from an ultrasound image being an image indicating a contour of the organ and being extracted from an image of the organ appearing in the ultrasound image; receiving, from a user of the ultrasound diagnostic device, specification information specifying a manual correction target ultrasound image among the ultrasound images and correction information indicating details of a manual correction that the user performs with respect to a first contour image extracted from the manual correction target ultrasound image; and correcting the first contour image extracted from the manual correction target ultrasound image according to the correction information to obtain a corrected first contour image. In the contour extraction method pertaining to one aspect of the present disclosure, in the extracting, in addition to the first contour image being extracted from each of the ultrasound images, a second contour image is extracted from a target ultrasound image among the ultrasound images by using information indicating the corrected first contour image, the target ultrasound image differing from the manual correction target image.

The contour extraction method pertaining to one aspect of the present disclosure achieves the same effects as the ultrasound diagnostic device pertaining to one aspect of the present disclosure.

Various aspects as described above, which include both those that are general and those that are specific, may be implemented as a system, a method, an integrated circuit, a computer program, or a computer-readable recording medium such a CD-ROM, or may be implemented as a combination of any of a system, a method, an integrated circuit, a computer program, and a computer-readable recording medium.

In the following, detailed description is provided on embodiments of the present disclosure, with reference to the accompanying drawings.

Note that the embodiments merely provide description on examples, which include both those that are general and those that are specific. Thus, the numbers, the shapes, the materials, the constituent elements, the arrangement of the constituent elements, the connection between the constituent elements, the steps, the order in which steps are performed, etc., described in the embodiments should be construed as being non-limiting examples. Further, beside those recited in the independent claims, which describe the broadest of concepts, constituent elements appearing in the embodiments are to be construed as being optional.

Embodiment 1

In the following, description is provided on an ultrasound diagnostic device and a method pertaining to embodiment 1, with reference to the accompanying drawings. An ultrasound diagnostic device 1 pertaining to embodiment 1 automatically extracts blood vessel contour images from a plurality of spatially-successive ultrasound images. The ultrasound diagnostic device 1 is characterized for performing correction of the blood vessel contour images such that, when a user manually corrects a given frame, the ultrasound diagnostic device 1 automatically corrects a plurality of neighboring frames by newly extracting blood vessel contour images from the neighboring frames. Note that in the present embodiment, description is provided while taking a blood vessel as one example of an organ, and while taking a blood vessel contour image as one example of a contour image of an organ.

Figure 1:
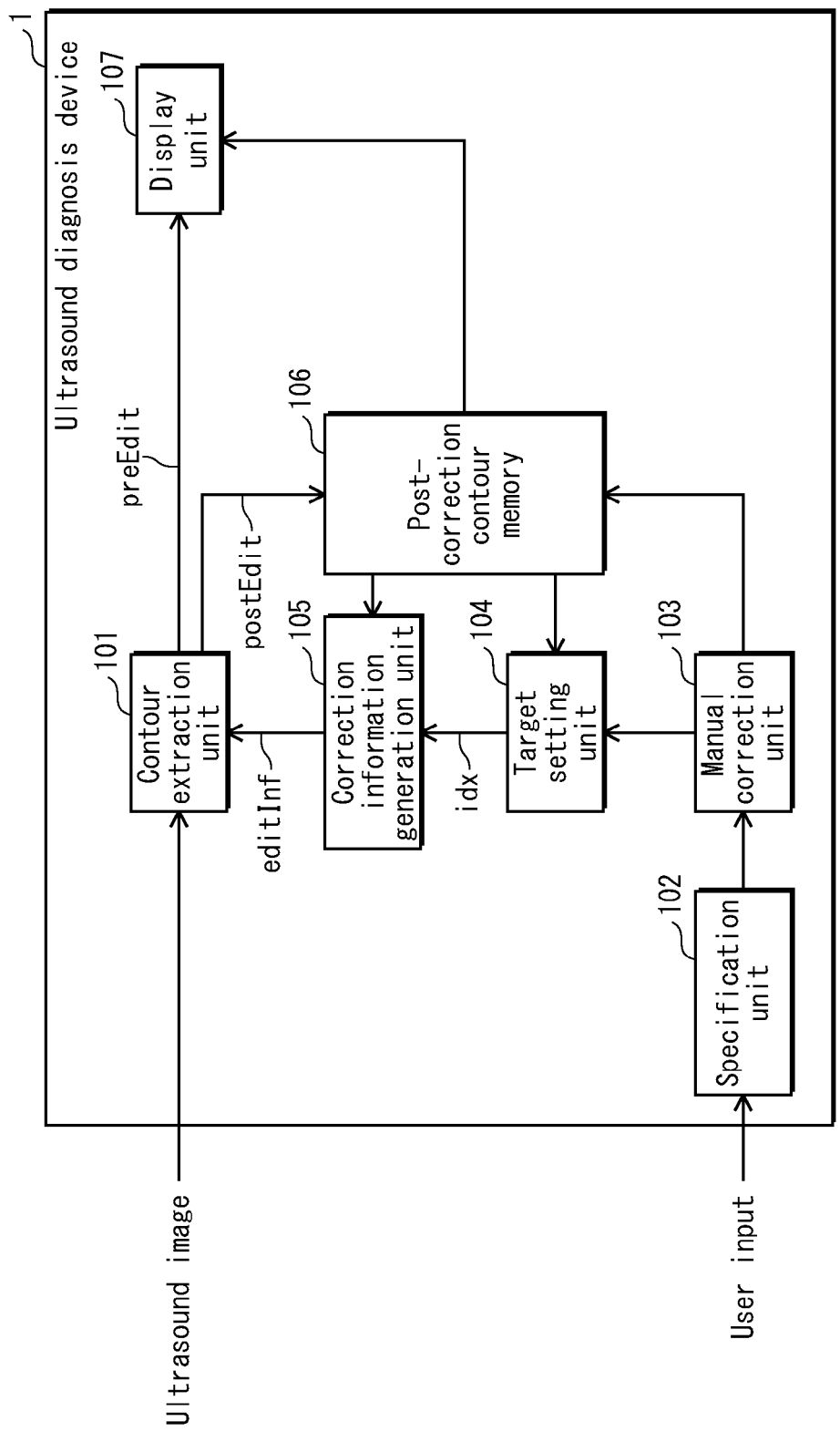
FIG. 1 is a block diagram illustrating the structure of an ultrasound diagnostic device pertaining to embodiment 1.

FIG. 1 is a block diagram illustrating the structure of the ultrasound diagnostic device 1. As illustrated in FIG. 1, the ultrasound diagnostic device 1 includes: a contour extraction unit 101; a specification unit 102; a manual correction unit 103; a target setting unit 104; a correction information generation unit 105; a post-correction contour memory 106; and a display unit 107.

The contour extraction unit 101 extracts blood vessel contour images (pre-correction contour images "preEdit") from a plurality of spatially-successive ultrasound images. The contour extraction is performed by first setting an initial contour image as a blood vessel contour image, and by iteratively updating the blood vessel contour image until the blood vessel contour image reaches either the tunica intima boundary or the tunica adventitia boundary of the blood vessel. Here, an initial contour image is an image indicating the approximate position and shape of the blood vessel. More specifically, an initial contour image in a given frame may be set according to (i) ultrasound blood flow information, (ii) a result of contour extraction performed with respect to a spatially-adjacent frame, or (iii) a specification made by the user of a specific area within the blood vessel. As the blood flow information, ultrasound color flow information, ultrasound power Doppler information, or ultrasound pulse Doppler information may be used. Typically, the closer an initial contour image set to a frame is to the actual contour of the blood vessel appearing in the frame, the more correct the blood vessel contour image extracted from the frame as a result of contour extraction is.

For example, the contour extraction unit 101 sets an initial contour image by regarding an area of a power Doppler image where signal intensity equals or exceeds a predetermined threshold value as an area where blood flow exists. The contour extraction unit 101, based on an initial contour image set to a given frame as described above, performs a search for the contour of the blood vessel in the given frame by employing an active contour method such as "Snakes" or the Level Set Method. Specifically, the contour extraction unit 101 searches for the contour of the tunica intima of the blood vessel or a contour of the tunica adventitia of the blood vessel, as the contour of the blood vessel. Here, note that the method according to which the search is performed is not particularly limited to an active contour method. That is, for example, the contour extraction unit 101 may perform contour extraction by searching for edges starting from an initial contour image and proceeding to areas located further inside or further outside the initial contour image as the search progresses. In such a case, the iterative updating of a blood vessel contour image need not be performed. Alternatively, an initial contour image may be, for example, information indicating a position of the contour of the blood vessel, such as a contour point (one point along the contour of the blood vessel).

The display unit 107 displays the contour images extracted by the contour extraction unit 101. For example, the display unit 107 displays the extracted contour images (pre-correction contour images "preEdit") so as to be overlaid on the ultrasound images. The user, by referring to what is displayed by the display unit 107, checks whether or not one or more of the blood vessel contour images extracted by the contour extraction unit 101 need to be corrected. When judging that a given one of the blood vessel contour images extracted by the contour extraction unit 101 needs to be corrected, the user manually corrects the given blood vessel contour image. In the following, description is provided on the functions of the functional blocks of the ultrasound diagnostic device 1 when the ultrasound diagnostic device 1 performs manual correction.

The specification unit 102 receives, from the user, specification information and correction information. The specification information specifies a frame (a manual correction target ultrasound image) with respect to which manual correction of a blood vessel contour image is to be performed. The correction information specifies the details of the correction to be performed with respect to the specified frame.

The manual correction unit 103 corrects a blood vessel contour image in the frame specified by the specification information received from the user according to the correction information received from the user. Further, the manual correction unit 103 stores the result of the correction to the post-correction contour memory 106. In addition, the manual correction unit 103 inputs, to the target setting unit 104, information identifying the frame with respect to which manual correction has been performed.

The target setting unit 104 specifies a frame (a target ultrasound image) with respect to which correction of a contour image (extraction of a second blood vessel contour image) is to be performed. Here, the target setting unit 104 specifies a frame close to the frame with respect to which manual correction has been performed. Further, the target setting unit 104 inputs identification information "idx" identifying the specified frame to the correction information generation unit 105.

The correction information generation unit 105 generates a correction initial contour image "editInf" that is to be used as initial information in the correction of the blood vessel contour image in the frame corresponding to the identification information "idx". Further, the correction information generation unit 105 outputs the correction initial contour image "editInf" to the contour extraction unit 101.

The contour extraction unit 101 extracts a blood vessel contour image from the frame corresponding to the identification information "idx", this time according to the correction initial contour image "editInf". Further, the contour extraction unit 101 stores the blood vessel contour image so extracted to the post-correction contour memory 106 as a post-correction contour image "postEdit".

The display unit 107 refers to the post-correction contour memory 106 and displays information on the post-correction contour image.

Here, it should be noted that the closer the shape of an initial contour image is to the actual shape of the contour of the blood vessel appearing in the frame, the more readily a correct blood vessel contour image is extracted from the frame. By using the result of manual correction, setting is possible of an initial contour image having a shape close to the actual shape of the contour of the blood vessel to a given frame. Thus, the accuracy when performing contour extraction increases, and accordingly, a contour image correctly indicating the shape of the contour of the blood vessel appearing in the image is obtained.

Figure 2:
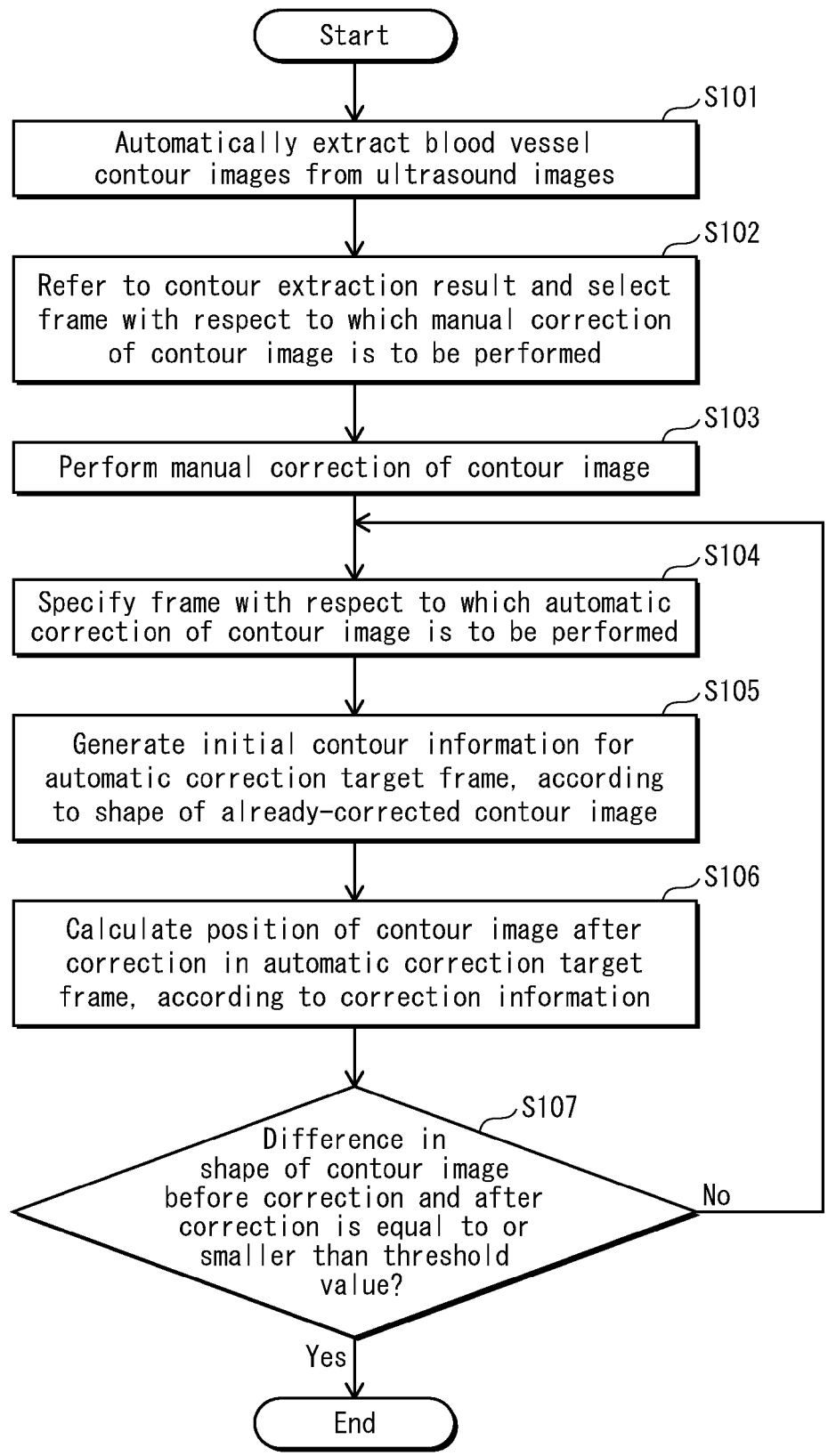
FIG. 2 is a flowchart illustrating the operations of the ultrasound diagnostic device pertaining to embodiment 1.

FIG. 2 is a flowchart illustrating the operations of the ultrasound diagnostic device 1.

In Step S101, the contour extraction unit 101 automatically extracts blood vessel contour images from a plurality of ultrasound images that are input.

In Step S102, the specification unit 102 receives, from the user, specification information for specifying a frame (a manual correction target ultrasound image) with respect to which manual correction of a contour image is to be performed and correction information for the specified frame. The specification unit 102 specifies the frame with respect to which manual correction of a contour image is to be performed by referring to the blood vessel contour images that are extracted by the contour extraction unit 101 in Step S101.

In Step S103, the manual correction unit 103 performs manual correction of a blood vessel contour image included in the specified frame according to the correction information received from the user.

Subsequently, through the execution of Steps S104 through S107, the ultrasound diagnostic device 1 performs automatic correction of a blood vessel contour image in a frame close to the frame with respect to which manual correction is performed in Step S103. In the following, detailed explanation is provided of each of Steps S104 through S107.

In Step S104, the target setting unit 104 specifies an automatic correction target frame (a target ultrasound image), which is a frame with respect to which automatic correction of a blood vessel contour image (extraction of a second blood vessel contour image) is to be performed. For example, the target setting unit 104 specifies, as automatic correction target frames, frames that are spatially-close to the manual correction frame (the frame with respect to which manual correction is performed in Step S103), one-by-one in the order of closeness to the manual correction frame. Here, note that the target setting unit 104 may specify one of the ultrasound images that are input as the automatic correction target frame. Further, the target setting unit 104 may specify, as the automatic correction target frame, one or more of the input ultrasound images that are each obtained from a position that is within a predetermined distance from an examination position from which the manual correction frame is obtained.

In Step S105, the correction information generation unit 105 generates a correction initial contour image "editInf" corresponding to the automatic correction target frame according to the result of manual correction or a blood vessel contour image resulting from a past iteration of automatic correction.

In Step S106, the contour extraction unit 101 performs contour extraction with respect to the automatic correction target frame according to the correction initial contour image "editInf", and calculates the shape of the blood vessel contour image extracted as a result of the automatic correction.

Here, note that the extraction of a blood vessel contour image performed in Step S101 and the extraction of a blood vessel contour image performed in Step S106 differ at least in terms of the initial contour image used. However, other parameters may also be provided with different values between Step S101 and Step S106. For example, when using brightness information of ultrasound B-mode images for the detection of contour images, the detection of a contour image is typically performed by applying a threshold to the amount of change in brightness observed near the contour, and further, while taking into consideration factors such as the continuity with neighboring contour. According to this, in the automatic extraction of contour images, it is likely that the actual contour exists near an initial contour indicated by correction initial contour image "editInf". Thus, when performing automatic extraction, estimation can be performed of the amount of change in brightness to be observed near the contour according to the distribution of brightness near the initial contour image, and the value obtained through such estimation can be used in the extraction of a blood vessel contour image. Note that the term "actual contour" refers to a contour image that correctly indicates the contour of the blood vessel appearing in an ultrasound image.

In Step S107, the target setting unit 104 determines whether or not the difference in shape of the contour image extracted from the automatic correction target frame before and after the automatic correction is equal to or smaller than a predetermined threshold value. When it is determined in Step S107 that the difference in shape of the contour image before and after the automatic correction is equal to or smaller than the predetermined threshold value, automatic correction is terminated. In contrast, when it is determined in Step S107 that the difference in shape of the contour image before and after the automatic correction exceeds the predetermined threshold value, a determination is made that automatic correction needs to be performed with respect to subsequent frames, and thus, processing returns to Step S104. Note that in the present disclosure, the relationship between frames, in addition to being indicated by referring to the positional relationship thereof, is also indicated by referring to the chronological order in which the frames are processed. For example, when taking two frames that are processed successively, one frame may be referred to as a previous or subsequent frame with respect to the other. Here, note that the determination in Step S107 of whether or not to terminate automatic correction may be performed according to other conditions. For example, the determination may be performed according to whether or not automatic correction has been performed with respect to a predetermined number of frames. Further, note that ultrasound images from each of which a blood vessel contour image has already been extracted may be input to the ultrasound diagnostic device 1. In such a case, the processing in Step S101 would become unnecessary, due to information related to the shapes of the contour images extracted in advance from the ultrasound images being input along with the ultrasound images. Further, note that the processing in Step S107 is not always necessary. In other words, modification may be made such that the determination in Step S107 is not performed. When making such a modification, the ultrasound diagnostic device 1, according to a result of manual correction performed with respect to one ultrasound image, extracts a second blood vessel contour image from only one other ultrasound image. Alternatively, a modification may be made such that, instead of the determination in Step S107, a determination is performed of whether or not the extraction of a second blood vessel contour image has been performed with respect to each and every one of the ultrasound images obtained. When making such a modification, the ultrasound diagnostic device 1, according to a result of manual correction performed with respect to one ultrasound image, extracts a second blood vessel contour image from each and every one of the ultrasound images other than the ultrasound image with respect to which the manual correction is performed.

Note that with reference to the flowchart in FIG. 2, explanation is provided on a method of automatically correcting, one-by-one, frames existing in either a positive direction or a negative direction from the manual correction frame along the direction in which the blood vessel runs, in the order of closeness to the manual correction frame. Alternatively, a modification may be made such that frames existing in both the positive direction and the negative direction from the manual correction frame are automatically corrected one-by-one, in the order of closeness to the manual correction frame. When making such a modification, the processing in Steps S104 through S107 is performed for each frame in each of the positive direction and the negative direction from the manual correction frame, until the difference in shape of the contour image extracted from the automatic correction target frame before and after the automatic correction equals or falls below the predetermined threshold value.

Figure 3:
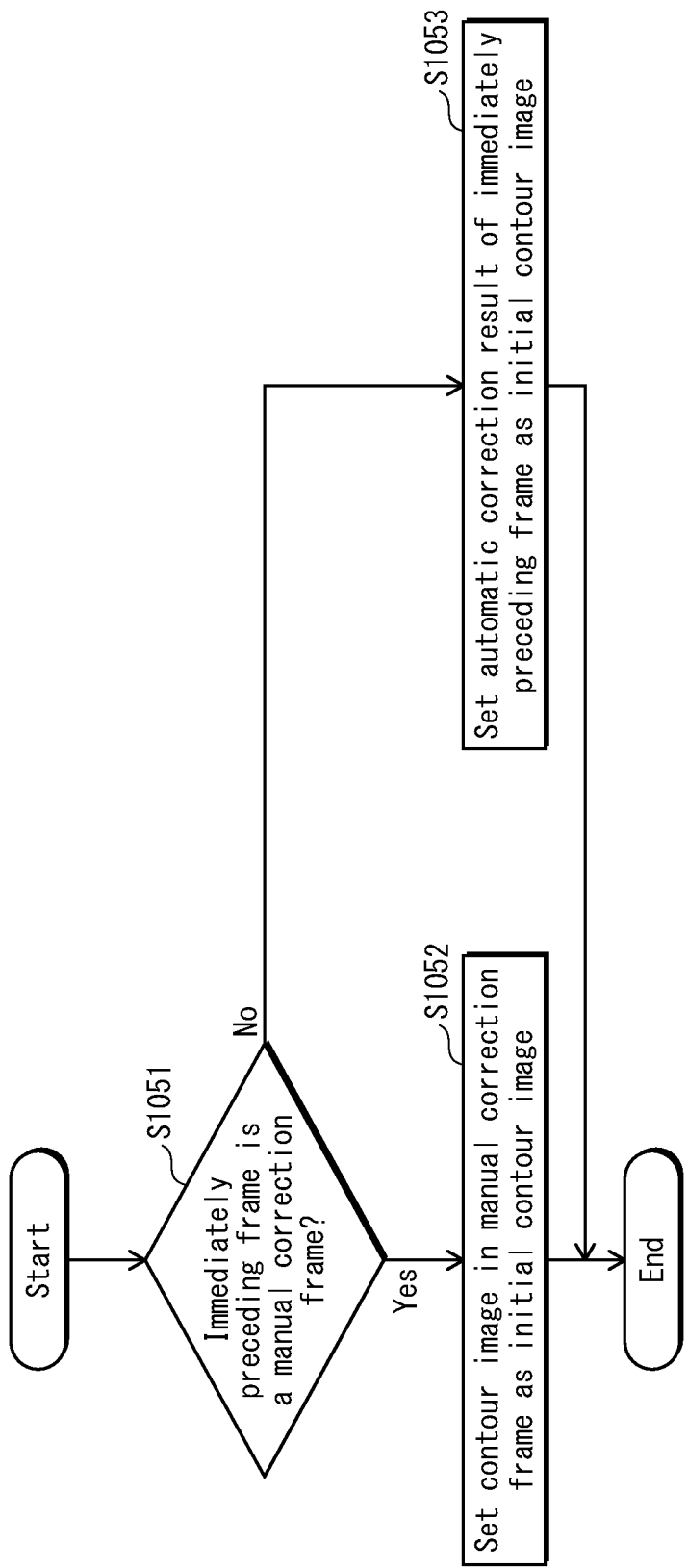
FIG. 3 is a flowchart illustrating processing in Step S105.

FIG. 3 is a flowchart illustrating processing in Step S105.

In Step S1051, the correction information generation unit 105 determines whether or not the frame immediately preceding the automatic correction target frame is the manual correction frame. When it is determined that the frame immediately preceding the automatic correction target frame is the manual correction frame, the blood vessel contour image in the manual correction frame is set as the correction initial contour image "editInf" (Step S1052). Meanwhile, when it is determined that the frame immediately preceding the automatic correction target frame is not the manual correction frame, the result of automatic correction of the contour image in the immediately preceding frame is set as the correction initial contour image "editInf" (Step S1053). In the above, in Steps S1052 and S1053, the corrected contour image of the manual correction frame or a contour image obtained as a result of automatic correction performed with respect to the immediately preceding frame is used as-is as the correction initial contour image "editInf" for the automatic correction target frame. However, a modification may be made such that (i) processing is performed of shifting the position of the contour image to be set as the initial contour image according to motion information indicating the movement between the immediately preceding frame and the automatic correction target frame or (ii) the change in the shape of the blood vessel wall between the immediately preceding frame and the automatic correction target frame is taken into consideration by detecting changes in pulsation between the frames.

Note that the ultrasound diagnostic device 1 may perform manual correction with respect to a plurality of frames. In such a case, when manual correction is performed with respect to multiple frames obtained from examination positions that are close to one another, there may be cases where the range of frames that are to be automatically corrected following manual correction of a given frame overlaps that for another frame. For instance, consider a case where manual correction is performed with respect to a $10^{th}$ frame and a $15^{th}$ frame. In such a case, when a configuration is made such that automatic correction is to be performed with respect to three frames preceding a manual correction frame and three frames succeeding the manual correction frame, the same frames (the $12^{th}$ frame and the $13^{th}$ frame) are included in both (i) the range of frames that are to be automatically corrected following manual correction of the $10^{th}$ frame and (ii) the range of frames that are to be automatically corrected following manual correction of the $15^{th}$ frame. In such a case where the ranges of frames that are to be automatically corrected for different manual correction frames overlap one another, a modification may be made such that automatic correction results obtained due to automatic correction being performed following manual correction of a manual correction frame is provided with different weights according to, for example, the spatial distance from the manual correction frame.

Further, although the present disclosure does not particularly restrict the manner in which the selection of a manual correction frame is to be performed, when correction needs to be performed with respect to a group of spatially-successive frames, a frame located near the center of the group may be selected as a manual correction frame. This is since the accuracy of automatic correction is higher for frames closer to the manual correction frame. Further, when correction needs to be performed with respect to a group of spatially-successive frames, the accuracy of automatic correction further improves when performing manual correction with respect to more than one frame in the group of frames.

In the above, description is provided on extraction and correction of blood vessel contour images without distinguishing between the tunica intima and the tunica adventitia of a blood vessel. For example, when examination is performed for detecting arteriosclerosis of the abdominal aorta, measurement is only performed of the diameter of the outer circumference of the tunica adventitia in many cases. Thus, in such a case, correction may be performed after extracting only contour images of the outer circumference of the tunica adventitia. Meanwhile, when examination is performed for detecting arteriosclerosis of the carotid artery, it is necessary to perform measurement of the thickness of the intima-media. Thus, in such a case, correction may be performed after extracting contour images of both the tunica intima boundary and the tunica adventitia boundary (i.e., the boundary of the inner circumference of the tunica adventitia).

Figure 4:
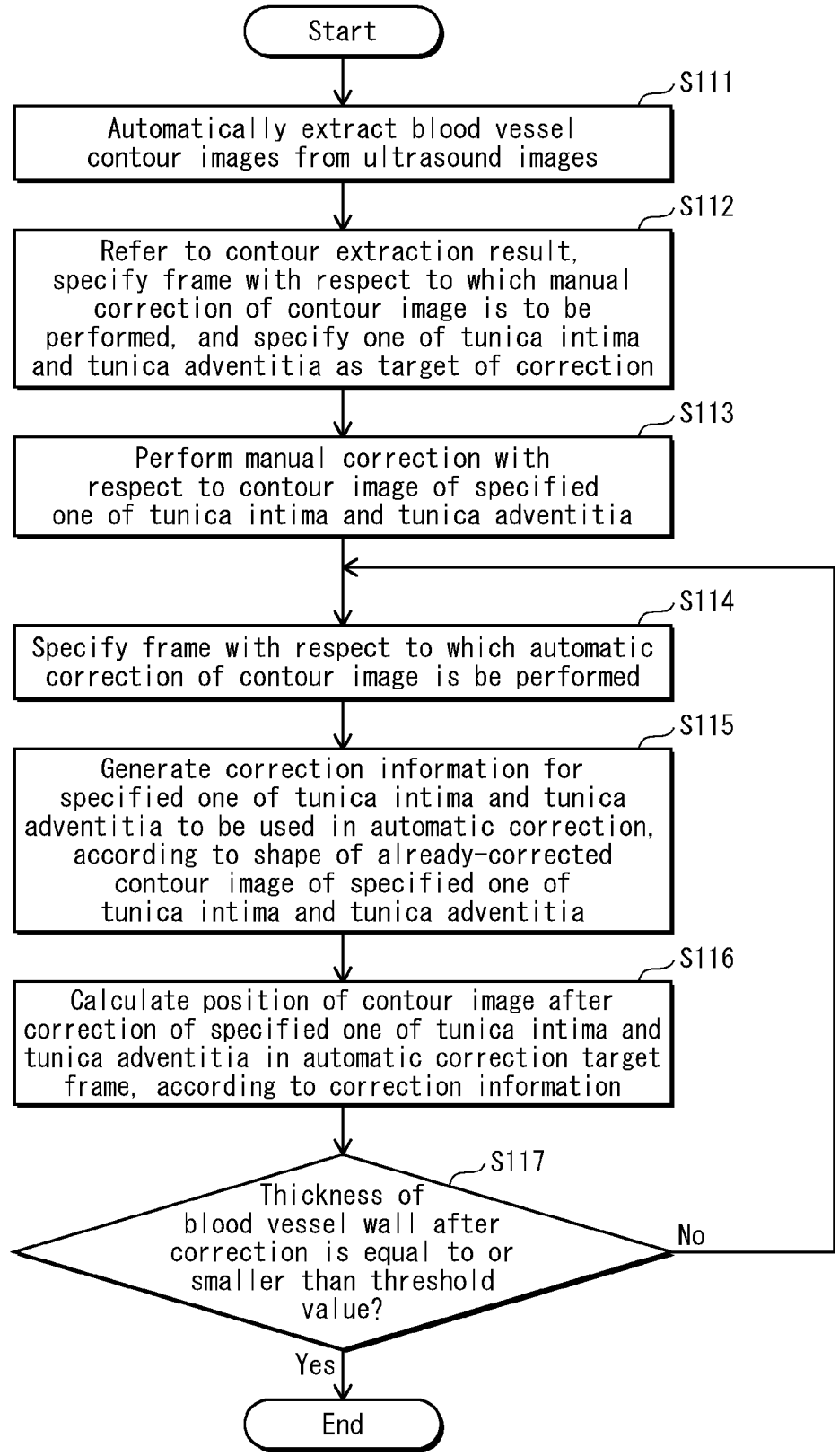
FIG. 4 is a flowchart illustrating processing performed with respect to both a tunica intima boundary and a tunica adventitia boundary.

FIG. 4 is a flowchart illustrating processing performed with respect to both the tunica intima boundary and the tunica adventitia boundary.

In Step S111, the contour extraction unit 101 extracts a contour image of the tunica intima (hereinafter referred to as an "tunica intima contour image") and a contour image of the tunica adventitia (hereinafter referred to as an "tunica adventitia contour image") from each of a plurality of ultrasound images that are input. Here, the contour extraction unit 101 may perform the extraction of tunica intima contour images and the extraction of tunica adventitia contour images according to different methods. For example, the contour extraction unit 101 may extract, as a tunica intima contour image, contour points obtained by shifting the result of contour extraction performed with respect to the tunica adventitia inwards by a predetermined thickness. Such a modification is made taking into account the fact that in many cases, the tunica intima is not clearly rendered in ultrasound images. Further, after determining the thickness of the intima-media in a manual correction frame according to the result of manual correction performed with respect to a tunica intima contour image and a tunica adventitia contour image, the contour extraction unit 101 may apply the thickness of the intima-media in the manual correction frame to adjacent frames such that the thickness of the intima-media in the adjacent frames gradually decreases as the distance from the manual correction frame increases. For example, the contour extraction unit 101 may determine the thickness of the intima-media in the adjacent frames according to a Gaussian function. Here, note that the thickness of the intima-media is set at multiple positions in the manual correction frame. For example, the thickness of the intima-media may be set at each vertex of the tunica adventitia or the tunica intima. Further, a modification may be made such that when manual correction is performed with respect to a plurality of frames, the thickness of the intima-media in adjacent manual correction frames is propagated, and further, such that weighting is provided when the adjacent manual correction frames overlap one another.

In Step S112, the ultrasound diagnostic device 1 refers to the results of contour extraction performed with respect to the tunica intima and tunica adventitia, and selects a manual correction target frame. Further, the ultrasound diagnostic device 1 determines whether or not correction is to be performed of each of the tunica intima contour image and the tunica adventitia contour image in the manual correction target frame.

In Step S113, the ultrasound diagnostic device 1 corrects either the tunica intima contour image or the tunica adventitia contour image in the manual correction target frame, according to user specification.

Subsequently, in Steps S114 through S117, the ultrasound diagnostic device 1 corrects either a tunica intima contour image or a tunica adventitia contour image in an automatic correction target frame. The correction performed in Steps S114 through S117 corresponds to the processing illustrated in the flowchart in FIG. 2 being performed with respect to both the inner image contour image and the tunica adventitia contour image. However, the correction performed in Steps S114 through S117 differs from the processing illustrated in the flowchart in FIG. 2 in terms of the condition under which automatic correction is terminated and how correction initial information "editInf" is generated. In the following, detailed description is provided on such differences.

In Step S117, the ultrasound diagnostic device 1 determines whether or not automatic correction is to be terminated. The ultrasound diagnostic device 1 calculates the thickness of the intima-media in the automatic correction target frame after the automatic correction according to the one of the tunica intima contour image and the tunica adventitia contour image that is determined as the target of correction in Step S112. Subsequently, the ultrasound diagnostic device 1 determines whether or not the thickness of the intima-media so calculated is smaller than or equal to a predetermined threshold value. When determining that the thickness of the intima-media is smaller than or equal to the predetermined threshold value, the ultrasound diagnostic device 1 terminates automatic correction. In contrast, when determining that the thickness of the intima-media is greater than the predetermined threshold value, the ultrasound diagnostic device 1 returns to the processing in Step S114. Here, as the thickness of the intima-media, the maximum thickness of the intima-media over the entire circumference of the blood vessel may be used. Further, when it is desired to examine the overall degree of thickening of the intima-media, an index value such as the average thickness of the intima-media over the entire circumference of the blood vessel or a median of the thickness of the intima-media over the entire circumference of the blood vessel may be used as the thickness of the intima-media. Further, the above-described threshold value applied to the thickness of the intima-media is set to a certain thickness that would necessitate a diagnosis that a plaque is formed or that thickening of the intima-media has occurred. Further, when performing the determination of whether or not to terminate automatic correction according to the thickness of the intima-media, it is desirable that automatic correction be performed with respect to both the tunica intima contour image and the tunica adventitia contour image in the automatic correction target image. As such, a modification may be made such that: (i) the determination in Step S117 is performed according to the thickness of the intima-media when, at the point of determination, both the tunica intima contour image and the tunica adventitia contour image in the automatic correction target image have been automatically corrected; and (ii) the determination in Step S117 is performed according to the method used in making a determination of termination in Step S107 in FIG. 2 when, at the point of determination, only one of the tunica intima contour image and the tunica adventitia image in the automatic correction target image has been automatically corrected.

As such, when manual correction is performed with respect to a given frame included in a plaque region of a blood vessel, the ultrasound diagnostic device 1 performs automatic correction with respect to frames preceding and succeeding the given frame, thereby correcting the contour of the entire plaque region. Typically, the boundary of the contour of the tunica intima tends to be unclear in ultrasound images obtained from a plaque region, and thus, detection of the contour of the tunica intima in such ultrasound images is difficult. Due to this, cases frequently occur where tunica intima contour images are not correctly extracted from such ultrasound images. In view of such a problem, the above-described method is effective since the contour of the entire plaque region is corrected.

Note that in the contour extraction performed in Step S111, when a region of the blood vessel that is actually in the normal state (i.e., the state of the blood vessel where thickening of the intima-media has not taken place) is erroneously detected as being in a state where thickening of the intima-media has taken place, the thickness of the intima-media is detected to be greater than it actually is. In view of such a case, a modification may be made such that the thickness of the intima-media at such a region is reduced through the correction. In such a case, modification may be made such that, instead of performing the determination of termination as described in Step S117, the determination of termination is performed by using the method described in Step S107 in FIG. 2. Alternatively, modification may be made such that the determination of termination is made by using both the determination of termination described in Step S117 and the method described in Step S107 in FIG. 2.

Figure 5A:
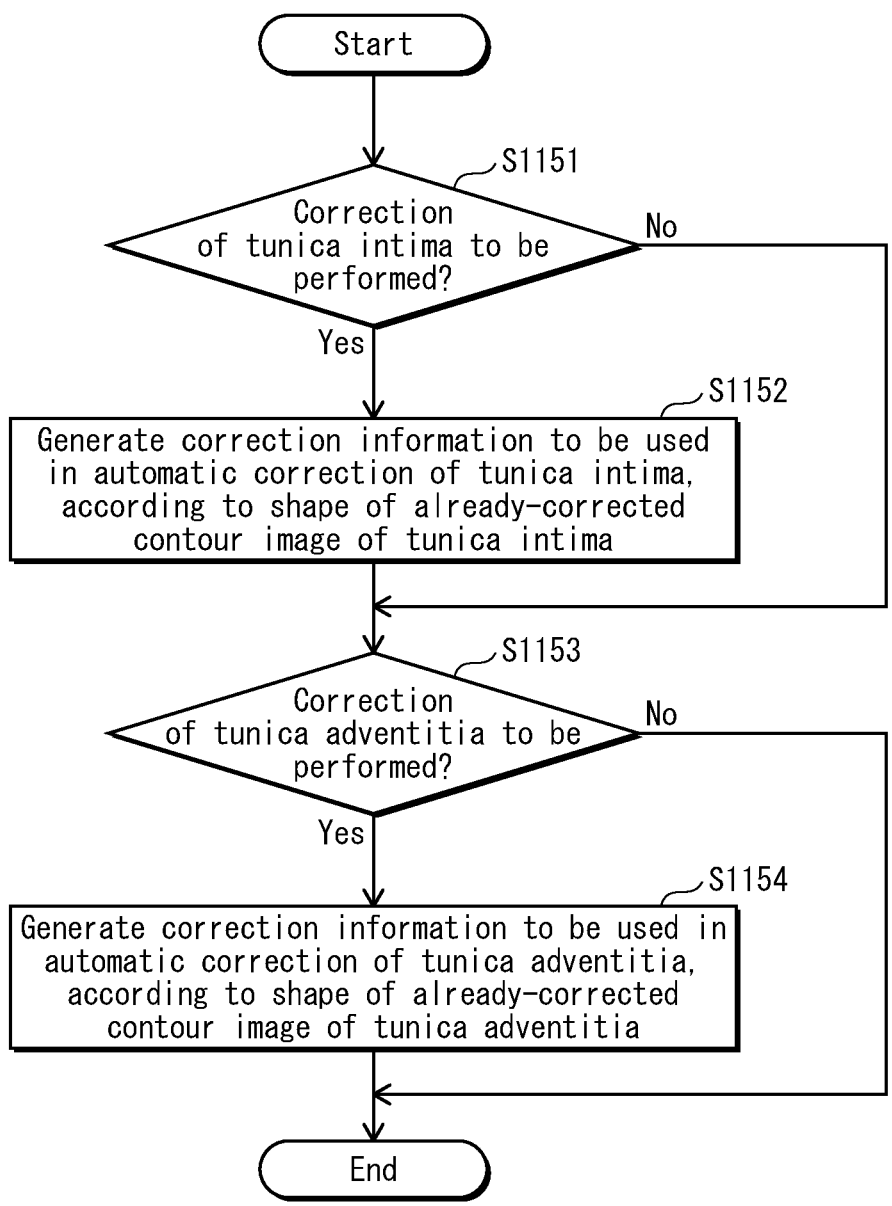
FIG. 5A is a flowchart illustrating a first method of generating correction initial information "editInf" that is used in automatic correction of a tunica intima and a tunica adventitia.
Figure 5B:
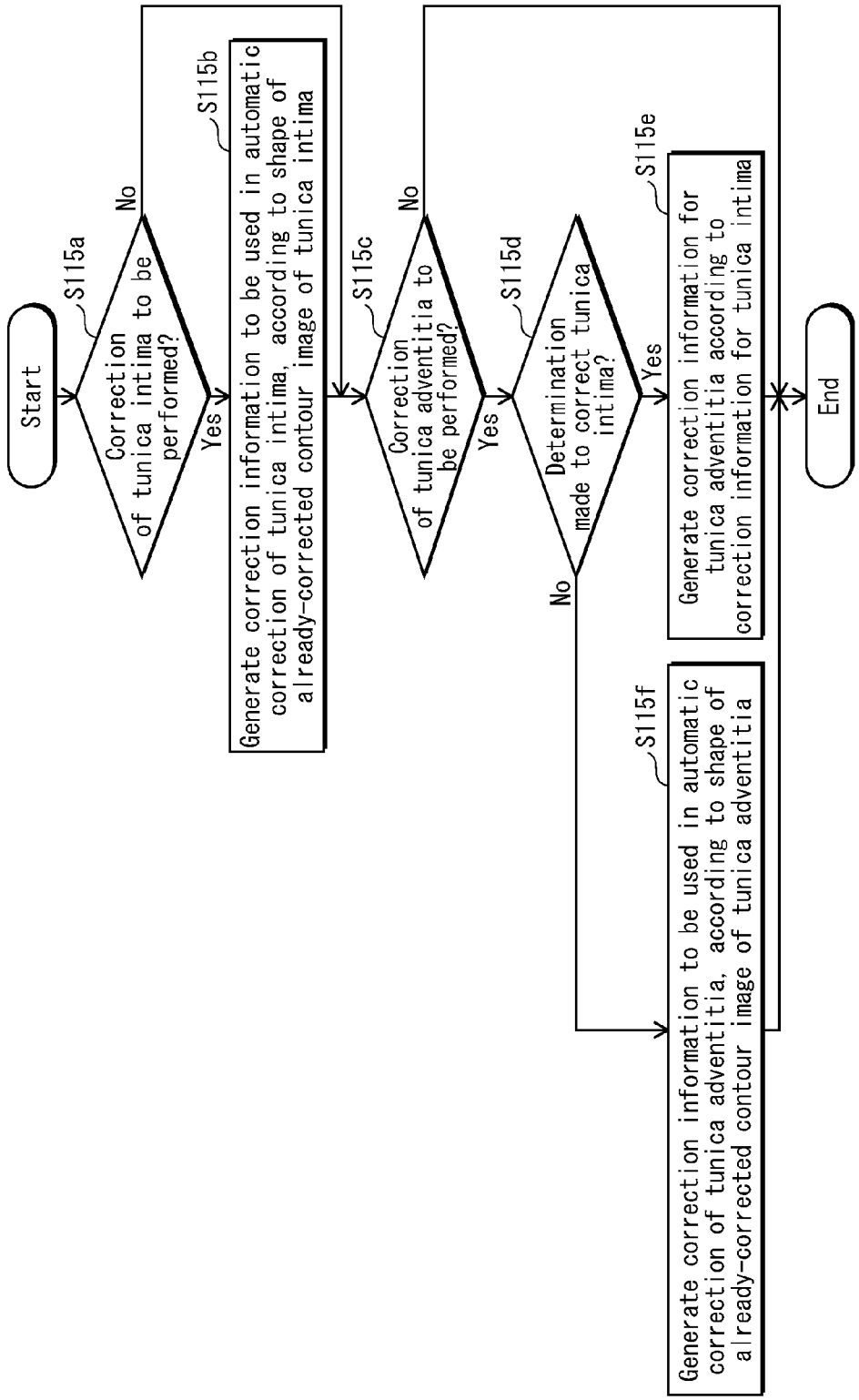
FIG. 5B is a flowchart illustrating a second method of generating the correction initial information "editInf" that is used in automatic correction of the tunica intima and the tunica adventitia.

Each of FIGS. 5A and 5B is a flowchart illustrating a method of generating correction initial information "editInf", which is used in performing automatic correction of a tunica intima contour image and a tunica adventitia contour image in Step S115. The method illustrated in FIG. 5A and the method illustrated in FIG. 5B differ from one another, and in the following, description is provided on each of the methods.

First, description is provided on the flowchart in FIG. 5A.

In Step S1151, a determination is made of whether or not to perform automatic correction of the tunica intima contour image in the automatic correction target frame. When determined that automatic correction of the tunica intima contour image is to be performed, processing proceeds to Step S1152. Meanwhile, when determined that automatic correction of the tunica intima contour image is not to be performed, processing proceeds to Step S1153.

In Step S1152, correction initial information "editInf" to be used in the automatic correction of the tunica intima contour image of the automatic correction target frame is generated according to the shape indicated by a tunica intima contour image obtained as a result of correction.

In Step S1153, a determination is made of whether or not to perform automatic correction of the tunica adventitia contour image in the automatic correction target frame. When determined that automatic correction of the tunica adventitia contour image is to be performed, processing proceeds to Step S1154. Meanwhile, when determined that automatic correction of the tunica adventitia contour image is not to be performed, processing is terminated.

In Step S1154, correction initial information "editInf" to be used in the automatic correction of the tunica adventitia contour image of the automatic correction target frame is generated based on the shape indicated by a tunica adventitia contour image obtained as a result of manual or automatic correction.

Next, description is provided on the flowchart in FIG. 5B.

In Step S115a, a determination is made of whether or not to perform automatic correction of the tunica intima contour image in the automatic correction target frame. When determined that automatic correction of the tunica intima contour image is to be performed, processing proceeds to Step S115b. Meanwhile, when determined that automatic correction of the tunica intima contour image is not to be performed, processing proceeds to Step S115c.

In Step S115b, correction initial information "editInf" to be used in the automatic correction of the tunica intima contour image in the automatic correction target image is generated based on the shape indicated by a tunica intima contour image obtained as a result of manual or automatic correction.

In Step S115c, a determination is made of whether or not to perform automatic correction of the tunica adventitia contour image in the automatic correction target frame. When determined that automatic correction of the tunica adventitia contour image is to be performed, processing proceeds to Step S115d. Meanwhile, when determined that automatic correction of the tunica adventitia contour image is not to be performed, processing is terminated.

In Step S115d, a determination is made of whether or not a determination is made to perform automatic correction of the tunica intima contour image in Step S115a. When determined that a determination is made to perform automatic correction of the tunica intima contour image, processing proceeds to Step S115e. Otherwise, processing proceeds to Step S115f.

In Step S115e, correction initial information "editInf" to be used in the automatic correction of the tunica adventitia contour image in the automatic correction target image is generated according to information on automatic correction of the tunica intima contour image. For example, correction initial information "editInf" to be used in the automatic correction of the tunica intima contour image in the automatic correction target frame may be used as correction information "editInf" to be used in the automatic correction of the tunica adventitia contour image in the automatic correction target frame. Alternatively, by making a modification such that automatic correction of the tunica intima contour image in the automatic correction target frame is completed before the execution of processing in Step S115e, in Step S115e, the tunica intima contour image obtained as a result of automatic correction may be used as correction information "editInf" to be used in the automatic correction of the tunica adventitia contour image in the automatic correction target frame.

In Step S115f, correction initial information "editInf" to be used in the automatic correction of the tunica adventitia contour image in the automatic correction target frame is generated based on the shape indicated by a tunica adventitia contour image obtained as a result of manual or automatic correction.

Note that in the flowchart in FIG. 5B and the description provided with reference to FIG. 5B, the "tunica intima" and the "tunica adventitia" may be replaced with one another.

Figure 6:
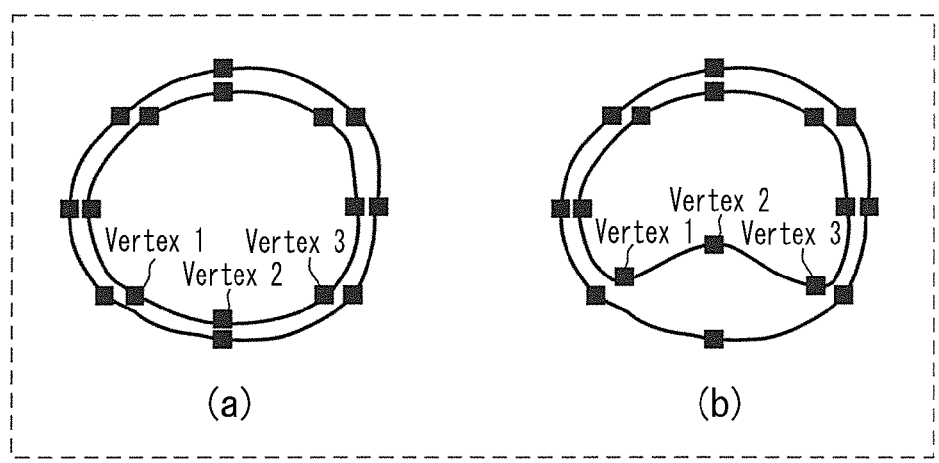
FIG. 6 is a diagram explaining an example of manual correction.

FIG. 6 is a diagram explaining an example of the manual correction. Portion (a) of FIG. 6 illustrates shapes of a tunica intima contour image and a tunica adventitia contour image before manual correction. Portion (b) of FIG. 6 illustrates the shape of the tunica intima contour image after manual correction. Here, manual correction is performed of correcting three vertices 1 through 3 of the tunica intima contour image.

In the manual correction, the user moves a plurality of vertices set along a target contour image by using a touch pen, a touch panel, or a user interface such as a mouse cursor. Thus, the shape of the contour image after manual correction is formed. Note that in the present disclosure, the term "correction information" refers to information on vertices indicating a shape of a contour image formed by manual correction, or to the contour image formed by manual correction.

Here, note that manual correction may be performed by the user creating a contour image by tracing the contour appearing in an image free-handedly, rather than by the user correcting a contour image by moving vertices of the contour image.

In FIG. 6, the tunica intima contour image and the tunica adventitia contour image are each illustrated to have eight vertices that are used in manual correction. Here, it should be noted that when creating a contour image, a greater or smaller number of vertices than used in manual correction may be used to create the shape of the contour image.

In the following, vertices of a contour image that are used in correction are referred to as "correction vertices", and vertices of a contour image other than those used in correction are referred to as "non-correction vertices". Here, it should be noted that the positions of the non-correction vertices can be generated by performing interpolation with respect to the correction vertices. For example, when generating one non-correction vertex by performing interpolation with respect to each adjacent pair of correction vertices, a total of sixteen vertices can be obtained, and the shape of a contour image may be formed by using such vertices when generating the contour image. Alternatively, the positions of non-correction vertices may be determined by generating an initial contour image according to the positions of the correction vertices in a contour image that has been corrected through manual correction, and then performing contour extraction. In such a case, the positions of the correction vertices are not updated in the contour extraction.

Figure 7A:
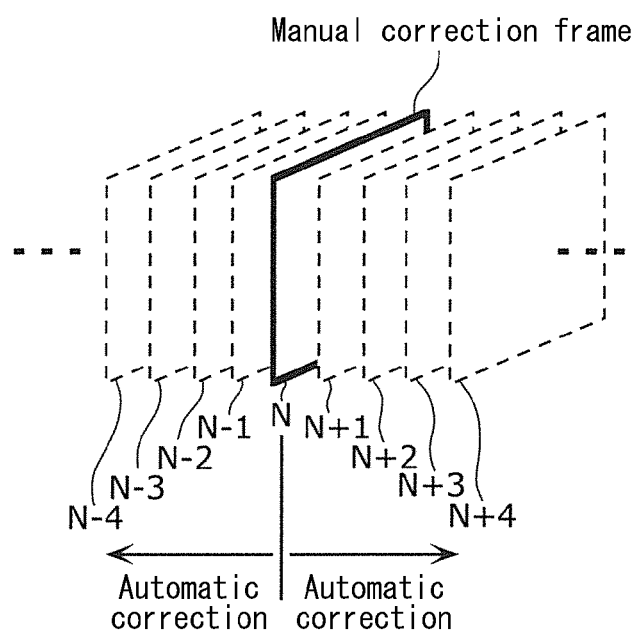
FIG. 7A is a first explanatory diagram illustrating an example of automatic correction processing of the tunica intima.

Each of FIGS. 7A and 7B is an explanatory diagram illustrating an example of processing in automatic correction of tunica intima contour images.

FIG. 7A shows how neighboring frames are automatically corrected when a frame N is manually corrected. In specific, blood vessel contour images in four frames (N+1, N+2, N+3, and N+4) in each of the positive direction and the negative direction from the frame N are automatically corrected.

FIG. 7B includes portions illustrating the shapes of contour images in the automatic correction target frames, before and after the automatic correction. Portion (a) of FIG. 7B illustrates a result of manual correction performed with respect to frame N. The manual correction is performed with respect to a tunica intima contour image in frame N. Portion (b) of FIG. 7B illustrates the shapes of contour images in frame N+1 before the automatic correction, and portion (c) of FIG. 7B illustrates the shapes of contour images in frame N+1 after the automatic correction. In the automatic correction performed with respect to frame N+1, a tunica intima contour image is extracted from frame N+1 by using, as an initial contour image, the tunica intima contour image obtained as a result of the manual correction performed with respect to frame N. Portion (d) of FIG. 7B illustrates the shapes of contour images in frame N+2 before the automatic correction, and portion (e) of FIG. 7B illustrates the shapes of contour images in frame N+1 after the automatic correction. In the automatic correction performed with respect to frame N+2, a tunica intima contour image is extracted from frame N+2 by using, as an initial contour image, the tunica intima contour image obtained as a result of the automatic correction performed with respect to frame N+1. As such, automatic correction is performed with respect to a given frame and a contour image is extracted from the given frame according to a shape of a contour image obtained as a result of manual correction or automatic correction already performed with respect to another frame.

Figure 8:
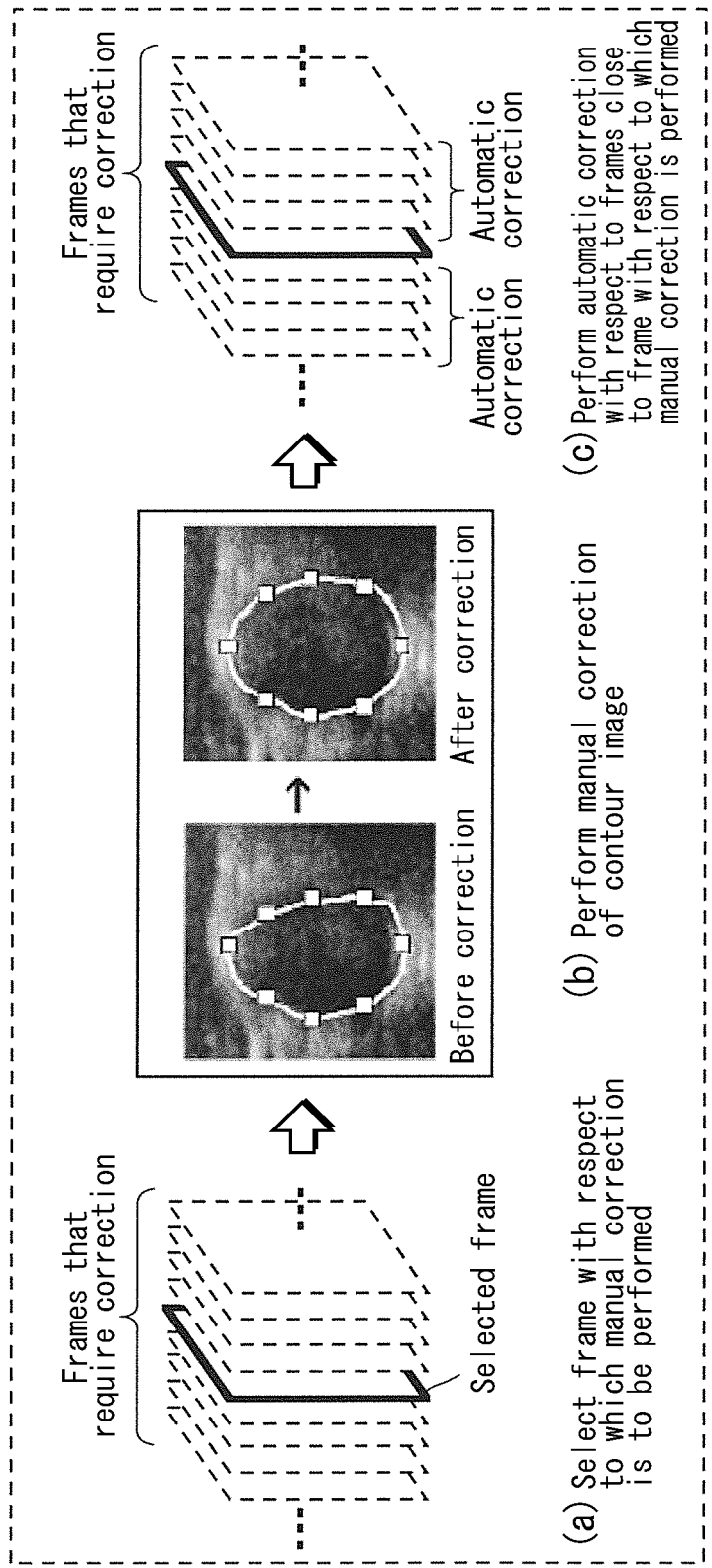
FIG. 8 is a diagram illustrating the effects of the ultrasound diagnostic device pertaining to embodiment 1.

FIG. 8 is a diagram illustrating the effects achieved by the ultrasound diagnostic device 1 pertaining to the present embodiment. Portion (a) of FIG. 8 illustrates an example of a selection of a manual correction target frame, and portion (b) of FIG. 8 illustrates an example of manual correction performed with respect to the selected frame. Portion (c) of FIG. 8 illustrates how neighboring frames of the manual correction frame are automatically corrected. The ultrasound diagnostic device 1 differs from the ultrasound diagnostic device 2300 pertaining to conventional technology in that there is no need of manually correcting each and every frame that needs to be corrected. This is since the ultrasound diagnostic device 1, when a given frame is manually corrected, automatically corrects blood vessel contour images in neighboring frames of the given frame. As such, the ultrasound diagnostic device 1 reduces the time required for contour correction by a great extent. In addition, when different users perform manual correction, differences are likely to be observed in the contour images obtained as a result of contour extraction and manual correction depending upon which of the users performed the manual correction. However, when automatically correcting extracted contour images as described in the present embodiment, the contour images obtained as result of contour extraction and automatic correction are stable, in the sense that not so much of a difference is observed between the contour images that are obtained.

As described above, the ultrasound diagnostic device pertaining to the present embodiment, when correction based on user specification (manual correction) is performed with respect to a first contour image of an organ extracted from a manual correction target ultrasound image among a plurality of ultrasound images, extraction of a second contour image from an ultrasound image other than the manual correction target ultrasound image is performed according to the result of the manual correction. Thus, the ultrasound diagnostic device pertaining to the present embodiment extracts a second contour image from an ultrasound image other than the manual correction target ultrasound image while applying the result of the manual correction performed by the user. That is, compared to conventional technology that requires users to perform manual correction with respect to each of a plurality of ultrasound images and thus necessitates a great amount of labor and time, the ultrasound diagnostic device pertaining to the present embodiment reduces the amount of labor and time required for correcting ultrasound images. Thus, the ultrasound diagnostic device pertaining to the present embodiment more accurately extracts contour images of an organ from a plurality of diagnostic images in a relatively short amount of time.

Further, the ultrasound diagnostic device pertaining to the present embodiment uses a corrected first contour image, obtained as a result of a user performing manual correction, as an initial contour image when extracting a second contour image from an ultrasound image other than a manual correction target ultrasound image. Thus, the ultrasound diagnostic device pertaining to the present embodiment extracts contour images that are even more accurate.

Further, the ultrasound diagnostic device pertaining to the present embodiment extracts, while applying the result of manual correction, a second contour image from an ultrasound image that is obtained from an examination position close to an examination position from which a manual correction target ultrasound image is obtained. A contour image included in an ultrasound image that is obtained from an examination position close to an examination position from which a manual correction target ultrasound image is obtained is likely to have a shape similar to that of a contour image included in the manual correction target ultrasound image. Thus, the ultrasound diagnostic device pertaining to the present embodiment extracts contour images that are even more accurate.

Further, the ultrasound diagnostic device pertaining to the present embodiment, when extracting a second contour image from a target ultrasound image by applying the result of manual correction, uses the second contour image as the result of extraction when the second contour image and a first contour image initially extracted from the target ultrasound image differ in shape by at least the predetermined level. Meanwhile, the ultrasound diagnostic device pertaining to the present embodiment, when the second contour image and the first contour image extracted from the target ultrasound image do not differ in shape by at least the predetermined level, uses the first contour image as the result of the extraction. Thus, the ultrasound diagnostic device pertaining to the present embodiments uses the second contour image as the result of the extraction only when the difference between the second contour image and the first organ contour image is great.

Further, the ultrasound diagnostic device pertaining to the present embodiment extracts a second contour image from another target ultrasound image while applying the result of correction performed with respect to the target ultrasound image. The target ultrasound image is corrected while applying the result of manual correction. Thus, the ultrasound diagnostic device pertaining to the present embodiment more accurately extracts contour images of an organ from a plurality of diagnostic images in a relatively short amount of time.

Further, the ultrasound diagnostic device pertaining to the present embodiment extracts a second contour image from another target ultrasound image while applying the result of correction performed with respect to the target ultrasound image. The other target ultrasound image is obtained from an examination position close to an examination position from which the target ultrasound image is obtained.

Further, the ultrasound diagnostic device pertaining to the present embodiment extracts a contour image from each of a plurality of ultrasound images, one image at a time in order of closeness, in terms of examination position, to a manual correction target ultrasound image, and in each iteration of the extraction, uses the result of the extraction performed in a previous iteration of the search for extracting a contour image in a present iteration.

Further, the ultrasound diagnostic device pertaining to the present embodiment corrects a contour image of a blood vessel, or corrects a contour image of the tunica intima or the tunica adventitia.

Further, the ultrasound diagnostic device pertaining to the present embodiment extracts a second contour image from each ultrasound image in which a thickness of a blood vessel layer obtained as a result of the extraction is greater than or equal to the predetermined threshold value. That is, the ultrasound diagnostic device pertaining to one aspect of the present disclosure performs the extraction of a second contour image only with respect to a plaque portion of the blood vessel.

Embodiment 2

In the following, description is provided on an ultrasound diagnostic device and a method pertaining to embodiment 2, with reference to the accompanying drawings. An ultrasound diagnostic device 2 pertaining to the present embodiment differs from the ultrasound diagnostic device 1 in that the ultrasound diagnostic device 2 forms and displays a 3D image of the blood vessel according to blood vessel contour images in ultrasound images, before or after correction. In the following, description is provided on each of the functions of the ultrasound diagnostic device 2 that are related to the forming of a 3D image. Since the rest of the functions of the ultrasound diagnostic device 2 are similar to those of the ultrasound diagnostic device 1, the same reference signs are provided to such functions and description thereon is omitted.

Figure 9:
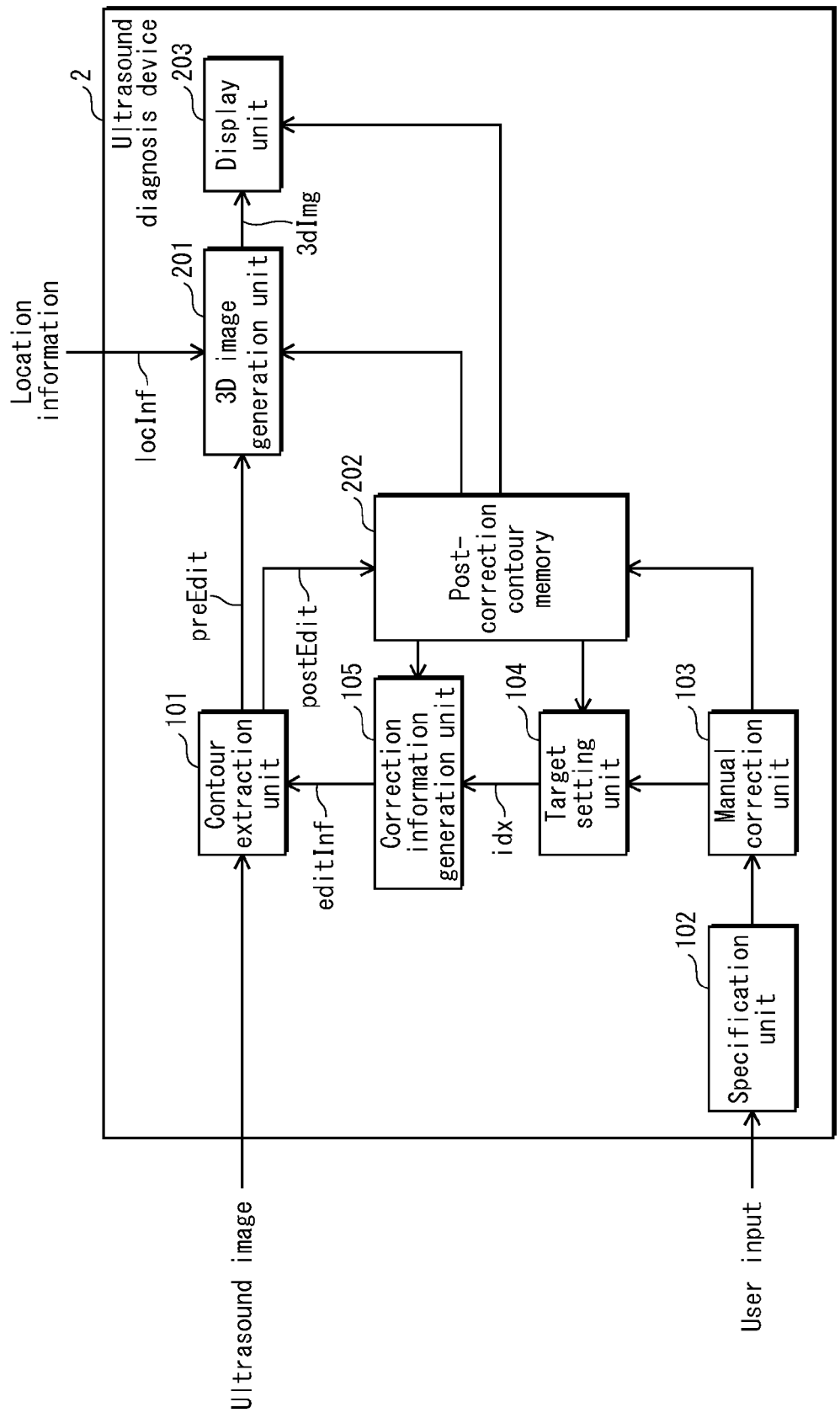
FIG. 9 is a block diagram illustrating the structure of an ultrasound diagnostic device pertaining to embodiment 2.

FIG. 9 is a block diagram illustrating the structure of the ultrasound diagnostic device 2 pertaining to the present embodiment. As illustrated in FIG. 9, the ultrasound diagnostic device 2 includes: the contour extraction unit 101; the specification unit 102; the manual correction unit 103; the target setting unit 104; the correction information generation unit 105; a post-correction contour memory 202; a 3D image generation unit 201; and a display unit 203.

The 3D image generation unit 201 generates a 3D image "3dImg" of a blood vessel according to pre-correction contour images "preEdit" and location information "locInf" indicating positions and orientations of the pre-correction contour images "preEdit". The location information "locInf" is acquired when ultrasound images are acquired, either at the same time as the ultrasound images are acquired or within a short period of time before or after the acquisition of the ultrasound images. For instance, the location information "locInf" is acquired by measuring a position and an orientation of an ultrasound probe when acquiring ultrasound images by using a magnetic sensor, an acceleration sensor, a gyroscope, a camera, etc. The ultrasound probe used for the acquisition of ultrasound images may be a 2D probe capable of acquiring 2D images or may be a 3D probe capable of acquiring 3D images. Further, among various types of 3D probes, the ultrasound probe used for the acquisition of ultrasound images may be an oscillation probe, which continuously acquires 2D ultrasound images by performing scanning while moving ultrasound transducers therein in an oscillating motion, or a matrix prove, which includes ultrasound transducers disposed in a 2D arrangement. When using a 3D probe as the ultrasound probe in the acquisition of ultrasound images, the location information "locInf" is generated by using the location information of the probe itself, and in addition, by taking into consideration a position and an orientation of a scan plane of the 3D probe when acquiring ultrasound images.

Here, note that the generation of a 3D image may be performed without acquiring location information by using an external means such as a sensor. As one example, a 3D image can be generated by acquiring ultrasound images by moving a probe in one direction at a fixed speed while the probe performs scanning. In such a case, although the accuracy is low compared to the above-described case, a 3D image can be generated since the relative positional relationship between adjacent ultrasound images would remain constant. As another example, if modeling of the shape of the examination subject is possible, the generation of a 3D image may be performed such that the 3D image matches the model. For example, a carotid artery typically has a Y shape. As such, when the examination subject is a carotid artery, a 3D image can be formed by arranging blood vessel contour images so as to form a Y shape in 3D. In the first example above, the location information "locInf" is determined according to scanning conditions, and in the second example, the location information "locInf" is determined according to a model of the shape of the examination subject.

Note that when correction of blood vessel contour images has already been performed, re-generation of a 3D image may be performed according to post-correction contour images "postEdit". Further, the post-correction contour images "postEdit" may be temporarily stored to the post-correction contour memory 202. Note that the location information "locInf" remains the same between post-correction contour images "postEdit" and pre-correction contour images "preEdit".

The display unit 203 displays the 3D image "3dImg" generated by the 3D image generation unit 201.

Figure 10:
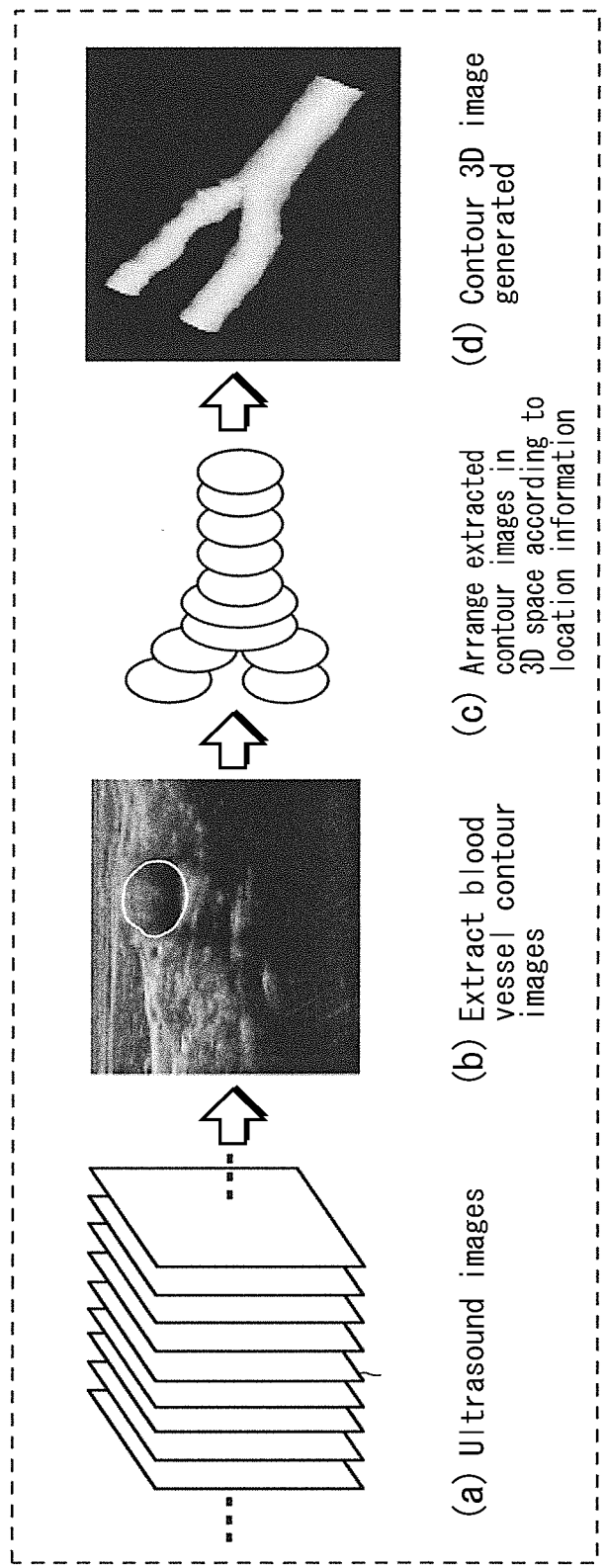
FIG. 10 is an explanatory diagram that illustrates the flow of processing up to generation and displaying of a 3D image.

FIG. 10 is an explanatory diagram that illustrates the flow of processing up to the generation and the displaying of the 3D image "3dimg". Portion (a) of FIG. 10 illustrates ultrasound images that are input. Blood vessel contour images are extracted from the ultrasound images (portion (b) of FIG. 10). Subsequently, the blood vessel contour images are arranged in a 3D space according to the location information (portion (c) of FIG. 10). Further, a 3D image so generated is displayed (portion (d) of FIG. 10).

Figure 11:
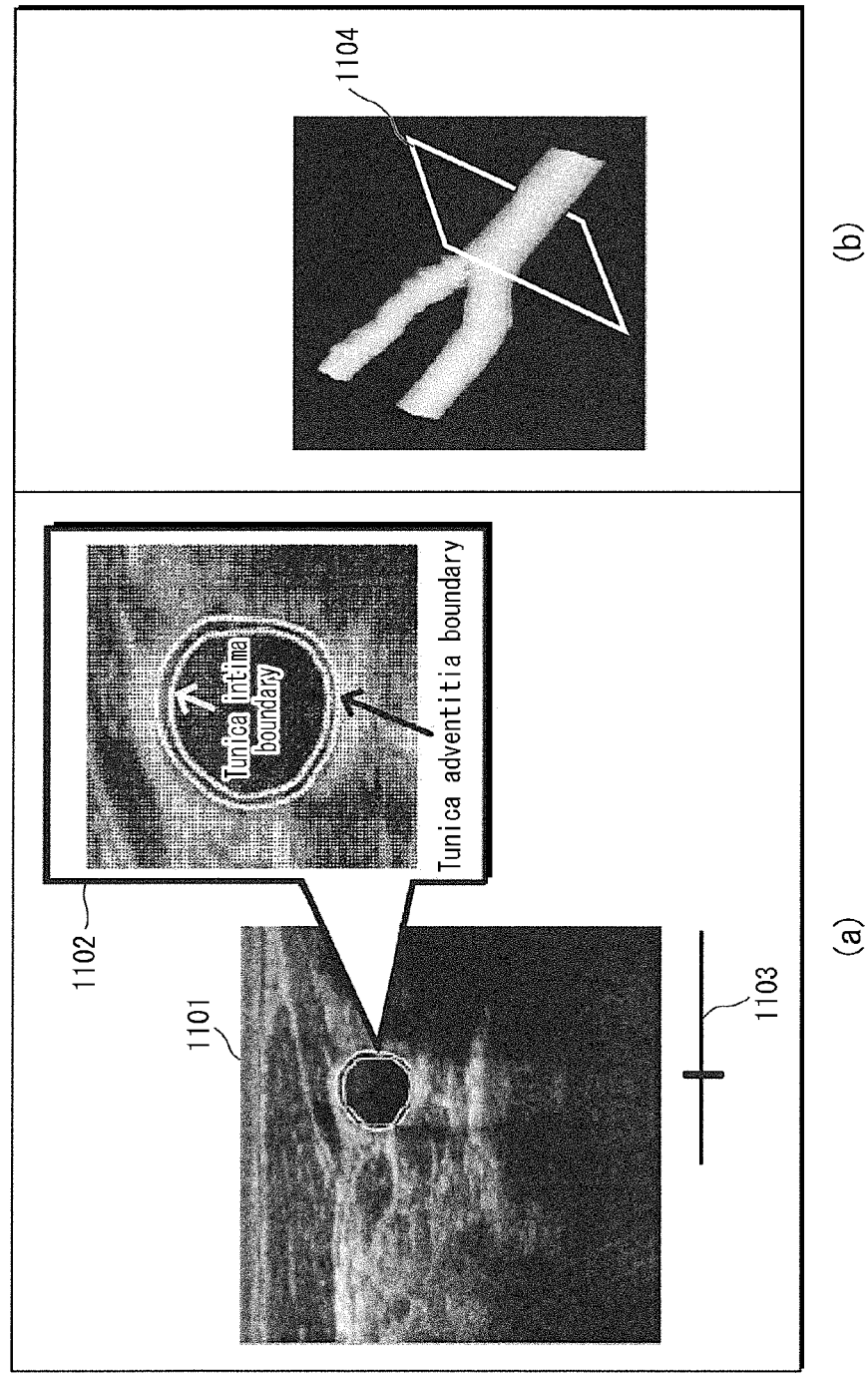
FIG. 11 is an explanatory diagram illustrating a first application example of the ultrasound diagnostic device pertaining to embodiment 2.

FIG. 11 is an explanatory diagram illustrating a first application example of the ultrasound diagnostic device 2 pertaining to the present embodiment. Portion (a) of FIG. 11 illustrates a screen for editing blood vessel contour images. In portion (a) of FIG. 11, the ultrasound diagnostic device 2 is displaying both a tunica intima contour image and a tunica adventitia contour image of a carotid artery, which are obtained as a result of automatic extraction, so as to be overlaid on an ultrasound B-mode image 1101. In addition, the ultrasound diagnostic device 2 may display a magnified image 1102 of the ultrasound B-mode image 1101.

On the screen for editing blood vessel contour images, the user of the ultrasound diagnostic device 2 performs correction with respect to either the tunica intima contour image or the tunica adventitia contour image as necessary. The user performs the correction freehandedly or by moving representative contour points of a contour image on the screen by performing certain operations, explanation of which is provided in the above with reference to FIG. 6. Portion (b) of FIG. 11 illustrates a display example of a 3D image of a contour of a blood vessel. The example illustrated in portion (b) of FIG. 11 is an example where the carotid artery has been scanned, and thus, a 3D image of the carotid artery, which has a Y shape, is being displayed. In portion (b) of FIG. 11, a rectangular frame 1104 is displayed so as to be overlaid onto the 3D image. The frame 1104 indicates a virtual plane indicating a scanning position at which the ultrasound image illustrated in portion (a) of FIG. 11 is acquired. In other words, an ultrasound image that is acquired when scanning the carotid artery at a position indicated by the virtual plane illustrated in portion (b) of FIG. 11 is displayed in portion (a) of FIG. 11. Here, a modification may be made such that the ultrasound image displayed in the screen at the left-hand side (portion (a) of FIG. 11) is switchable from one ultrasound image to another ultrasound image by moving the virtual plane. Alternatively, a modification may be made such that a slide bar 1103 is provided below the ultrasound image displayed in the screen, and the ultrasound image displayed in the screen (portion (a) of FIG. 11) is switchable from one ultrasound image to another ultrasound image by using the slide bar 1103.

Figure 12:
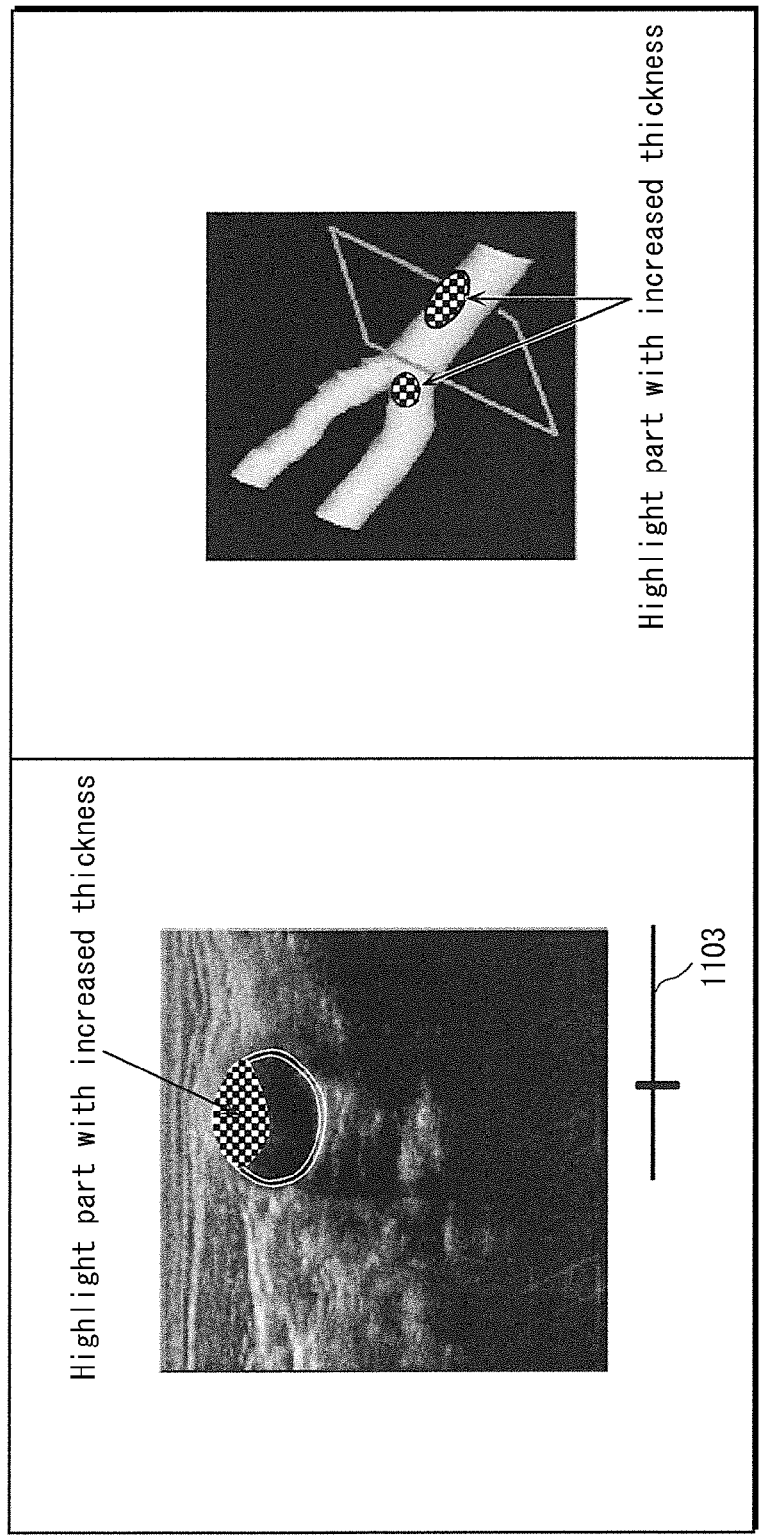
FIG. 12 is an explanatory diagram illustrating a second application example of the ultrasound diagnostic device pertaining to embodiment 2.

FIG. 12 is an explanatory diagram illustrating a second application example of the ultrasound diagnostic device 2 pertaining to the present embodiment. In FIG. 12, indication is provided of a part of a blood vessel where thickening of the intima-media has occurred on an ultrasound image and on a 3D image. Portion (a) of FIG. 12 illustrates a case where, in an ultrasound image, a part of the intima-media with increased thickness is highlighted. Portion (b) of FIG. 12 illustrates a case where, in a 3D image, a part of the intima-media with increased thickness is highlighted. In particular, by highlighting a part of the intima-media with increased thickness in a 3D image as in portion (b) of FIG. 12, the user can readily specify a part of the blood vessel with a disorder. Further, by highlighting a part of the intima-media with increased thickness in a 3D image, the user can use the ultrasound diagnostic device 2 to perform examination such as moving a virtual plane to a highlighted part of a 3D image and monitoring an ultrasound image corresponding to where the virtual plane is moved.

Figure 13:
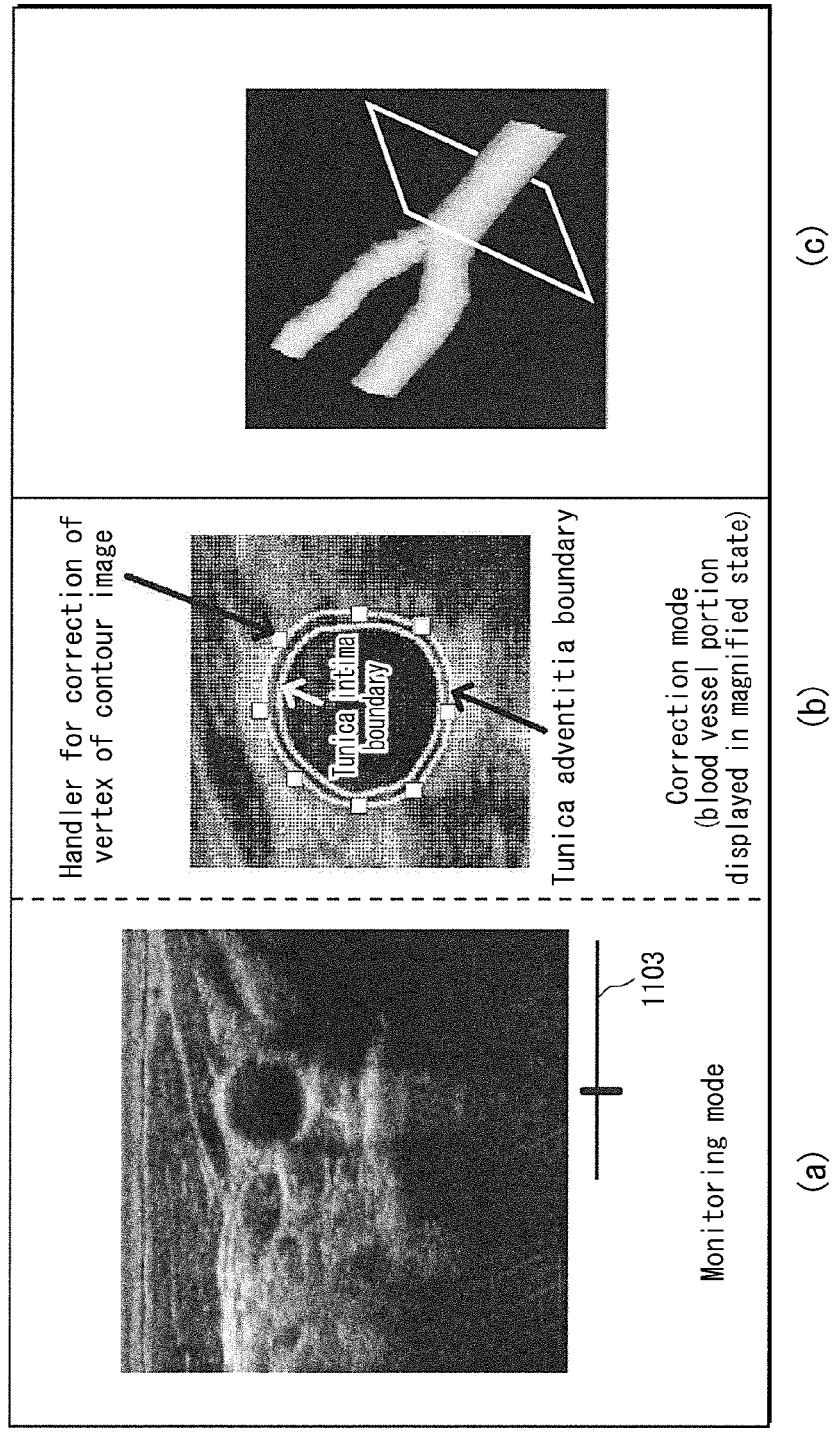
FIG. 13 is an explanatory diagram illustrating a third application example of the ultrasound diagnostic device pertaining to embodiment 3.

FIG. 13 is an explanatory diagram illustrating a third application example of the ultrasound diagnostic device 2 pertaining to the present embodiment. In the example illustrated in FIG. 13, to improve the usability of the ultrasound device 2 when the user performs contour correction, an entirety of an ultrasound image is displayed as illustrated in portion (a) of FIG. 13 when the user monitors an ultrasound image, and a blood vessel area of an ultrasound image is displayed in a magnified state as illustrated in portion (b) of FIG. 13 when the user performs correction of a blood vessel contour image. In addition, a 3D image of the blood vessel may also be displayed. Here, the 3D image may be a bird's eye image of a contour of the blood vessel as illustrated in portion (c) of FIG. 13. Also, in order to display the tunica intima boundary, the thickening of the intima-media, etc., to the user in a clearly recognizable state, a long-axis cross-sectional image, or a short-axis cross-sectional image, etc., of a contour of the blood vessel may be displayed. Further, conventional technology such as surface rendering, volume rendering, etc., is applicable for realizing displaying of 3D images.

Note that, besides technology related to 3D imaging, the application examples illustrated in FIGS. 11 through 13 can be implemented by using the ultrasound diagnostic device 1.

Further, to improve the visibility of shapes and statuses of contour images, a modification may be made of displaying tunica intima contour images and tunica adventitia contour images by using different colors, and/or of displaying pre-correction contour images and post-correction contour images by using different colors. In addition, a modification may be made such that the user is able to make a configuration of execution/non-execution of automatic correction of contour images.

Further, a modification may be made such that positions of vertices of contour images obtained as a result of manual correction and automatic correction are stored, and a contour image that reflects information editing having been previously performed is displayed when the user examines a same input ultrasound image for the second time. Further, a modification may also be made such that, when the user is to examine a same blood vessel region multiple times for certain purposes such as checking a chronological change in a plaque over years, the shape of the plaque observed in the previous examination is displayed in addition to the present shape of the plaque, whereby the user is enabled to compare the past and present shapes of the plaque.

Although description is provided above mainly focusing on a carotid artery as the examination subject, the ultrasound diagnostic device and method pertaining to the present disclosure is applicable to other blood vessels. For example, the ultrasound diagnostic device and method pertaining to the present disclosure is applicable to certain parts of the human body where arteriosclerosis frequently occurs, such as the abdominal aorta, the tibial arteries, the vertebral arteries, and the subclavian arteries. In addition, the ultrasound diagnostic device and method pertaining to the present disclosure is theoretically applicable to any tubular organ.

Further, the processing-target input images are not limited to being ultrasound images, and may be images acquired through computed tomography (CT), magnetic resonance imaging (MRI), etc. Further, a 3D image is readily acquirable when using technology such as CT, MRI, etc. As such, an ultrasound 3D image may be formed by mapping ultrasound images with respect to a 3D shape of a blood vessel acquired by application of such technology.

As description is provided up to this point, the ultrasound diagnostic device pertaining to the present embodiment enables putting together post-correction blood vessel contour images to form a 3D image of a blood vessel. Thus, the ultrasound diagnostic device pertaining to the present embodiment presents a 3D shape of a blood vessel to a user, which enables the user to intuitively acknowledge the contour of the organ (i.e., the blood vessel).

Embodiment 3

In the following, description is provided on an ultrasound diagnostic device pertaining to embodiment 3 and a method pertaining to embodiment 3, with reference to the accompanying drawings. An ultrasound diagnostic device 3 pertaining to embodiment 3 differs from the ultrasound diagnostic device 1 in that, when two or more post-correction blood vessel contour images that overlap one another exist in an ultrasound image, the ultrasound diagnostic device 3 merges the overlapping contour images into a single blood vessel contour image. In the following, description is provided on each of the functions of the ultrasound diagnostic device 3 that are related to the merging of blood vessel contour images. Since the rest of the functions of the ultrasound diagnostic device 3 are similar to those of the ultrasound diagnostic device 1, the same reference signs are provided to such functions and description thereon is omitted.

Figure 14:
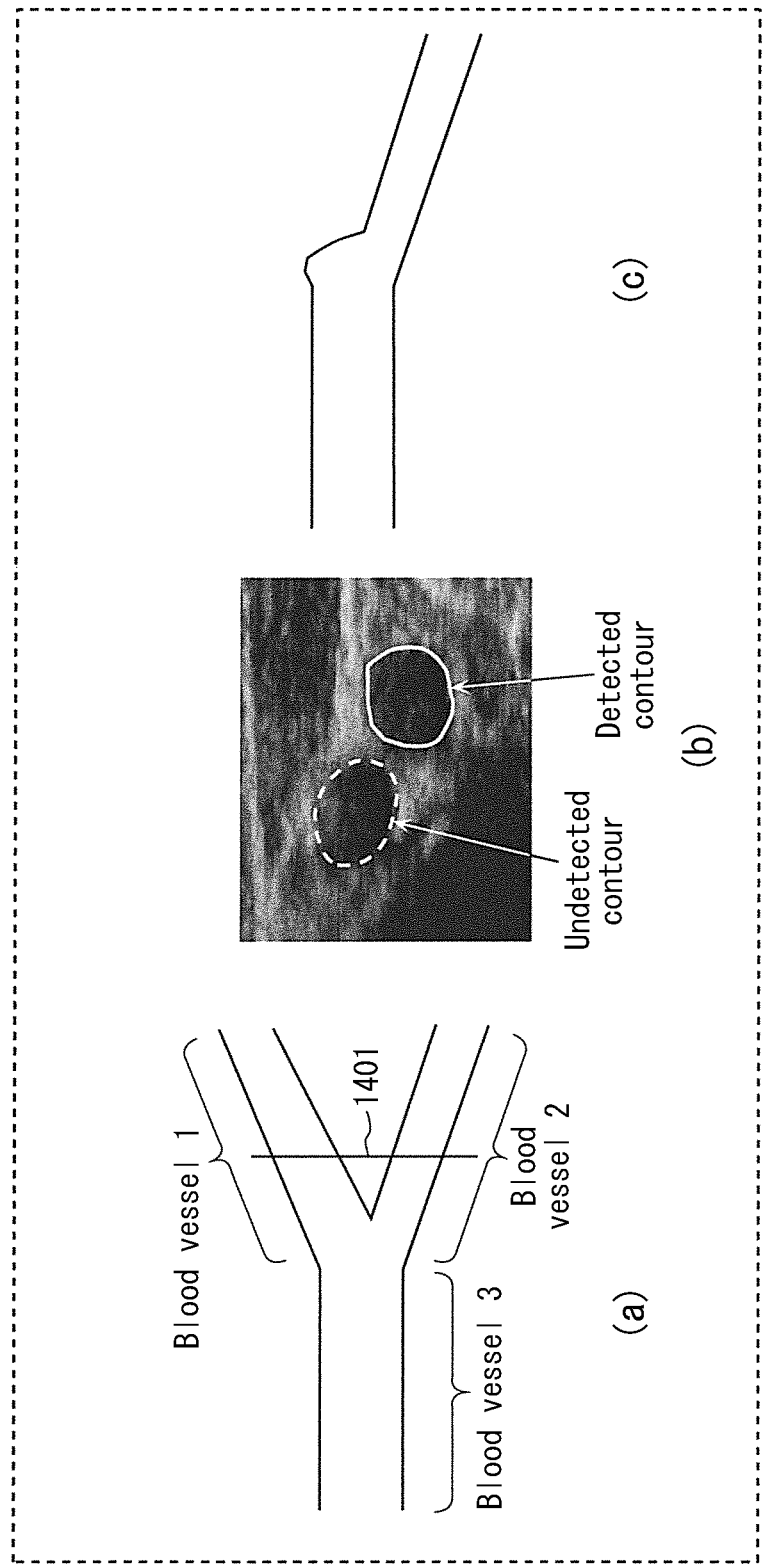
FIG. 14 is an explanatory diagram illustrating a situation that embodiment 3 takes into consideration.

FIG. 14 is an explanatory diagram that illustrates a situation that embodiment 3 takes into consideration. Portion (a) of FIG. 14 illustrates a blood vessel having a branching part (a blood vessel having a Y shape). The blood vessel is composed of a first blood vessel portion, a second blood vessel portion, and a third blood vessel portion, which are respectively indicated as blood vessel 1, blood vessel 2, and blood vessel 3 in portion (a) of FIG. 14. Such a Y-shaped blood vessel exists, for example, in the human carotid artery. An ultrasound image at a cross-sectional region 1401 of the Y-shaped blood vessel, obtained by an ultrasound diagnostic device, is illustrated in portion (b) of FIG. 14. Here, it should be noted that although the Y-shaped blood vessel includes, at the cross-sectional region 1401, the first blood vessel portion and the second blood vessel portion, when extraction of blood vessel contour images is performed with respect to the ultrasound image illustrated in portion (b) of FIG. 14, only one contour image corresponding to one of the two blood vessel portions may be extracted. When creating an image of the shape of the Y-shaped blood vessel by using the contour image so detected, the image of the Y-shaped blood vessel lacks the shape of the first blood vessel portion, which should be extending from the branching part, as illustrated in portion (c) of FIG. 14.

The ultrasound diagnostic device according to the present embodiment is able to acquire a correct shape of a blood vessel, even when contour images corresponding to a portion of the blood vessel are not detected through contour detection.

Figure 15:
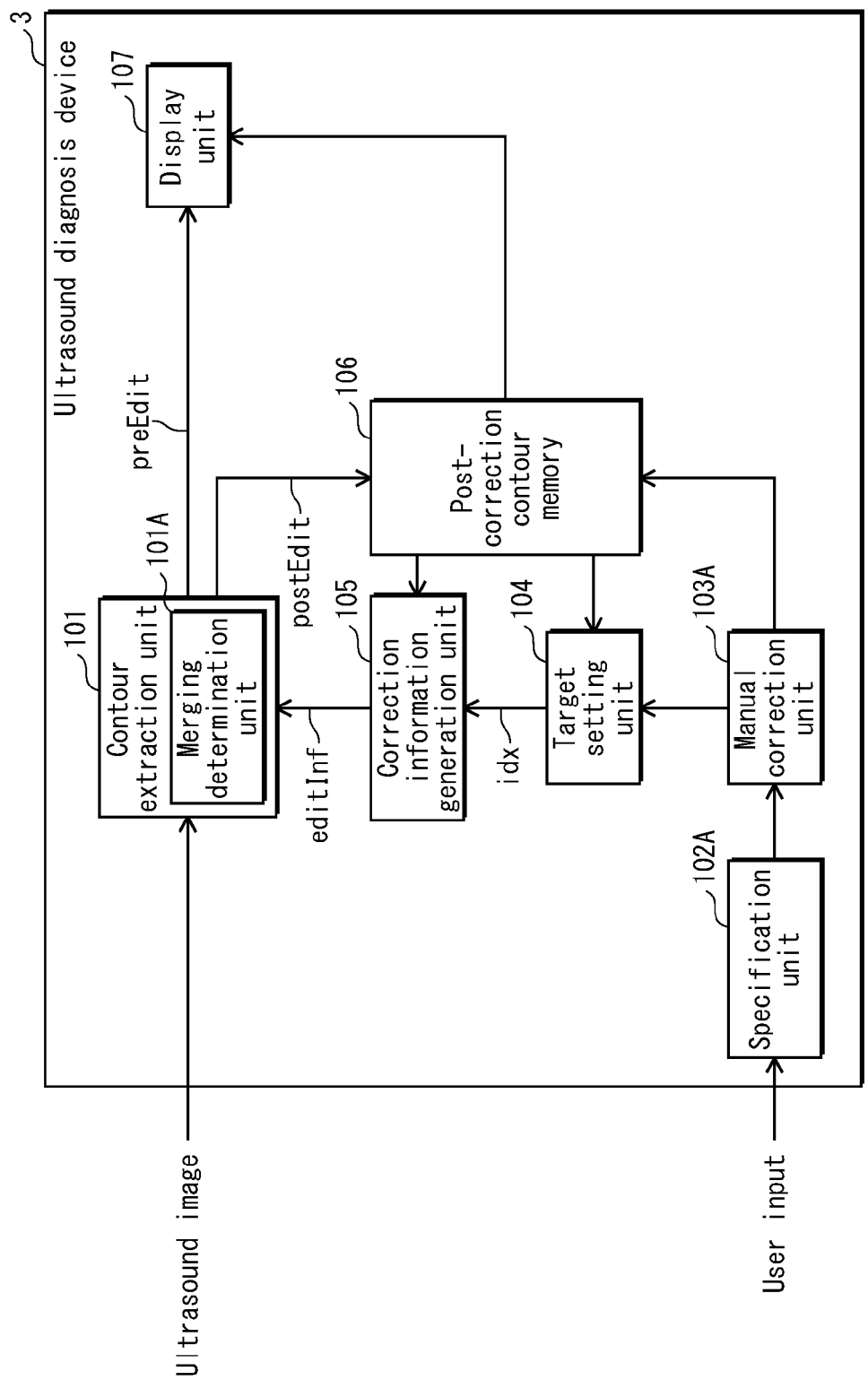
FIG. 15 is a block diagram illustrating the structure of an ultrasound diagnostic device pertaining to embodiment 3.

FIG. 15 is a block diagram illustrating the structure of the ultrasound diagnostic device 3 pertaining to the present embodiment. As illustrated in FIG. 15, the ultrasound diagnostic device 3 includes a specification unit 102A and a manual correction unit 103A. Further, the contour extraction unit 101 in the ultrasound diagnostic device 3 includes therein a merging determination unit 101A. Since functional blocks of the ultrasound diagnostic device 3 other than the contour extraction unit 101 are similar to those of the ultrasound diagnostic device 1, description thereof is omitted.

The specification unit 102A receives, from the user, specification information and correction information. The specification information specifies a frame (a manual correction target ultrasound image) with respect to which manual correction of a blood vessel contour image is to be performed. The correction information specifies the details of the correction to be performed with respect to the specified frame. Here, the specification unit 102A receives, as the correction information, information indicating a blood vessel contour image that has not been extracted from the specified frame by the contour extraction unit 101. For example, in the case of the example illustrated in portion (b) of FIG. 14, the specification unit 102A receives, as the correction information, information on the contour labeled as "undetected contour" in portion (b) of FIG. 14.

The manual correction unit 103A corrects blood vessel contour images in the frame specified by the specification information received from the user according to the correction information received from the user. Further, the manual correction unit 103A stores the result of the correction to the post-correction contour memory 106. In addition, the manual correction unit 103A inputs identification information identifying the frame with respect to which the manual correction has been performed to the target setting unit 104. Here, the manual correction unit 103A corrects the specified frame by newly creating a blood vessel contour image according to the information, included in the correction information, indicating a contour that has not been extracted from the specified frame by the contour extraction unit 101.

The merging determination unit 101A acquires contour images extracted by the contour extraction unit 101, and when two or more contour images overlapping one another are extracted from a given frame, creates a single contour image by merging the overlapping contour images. Further, the merging determination unit 101A stores the contour image so formed to the post-correction contour memory 106 as a post-correction contour image "postEdit".

Figure 16:
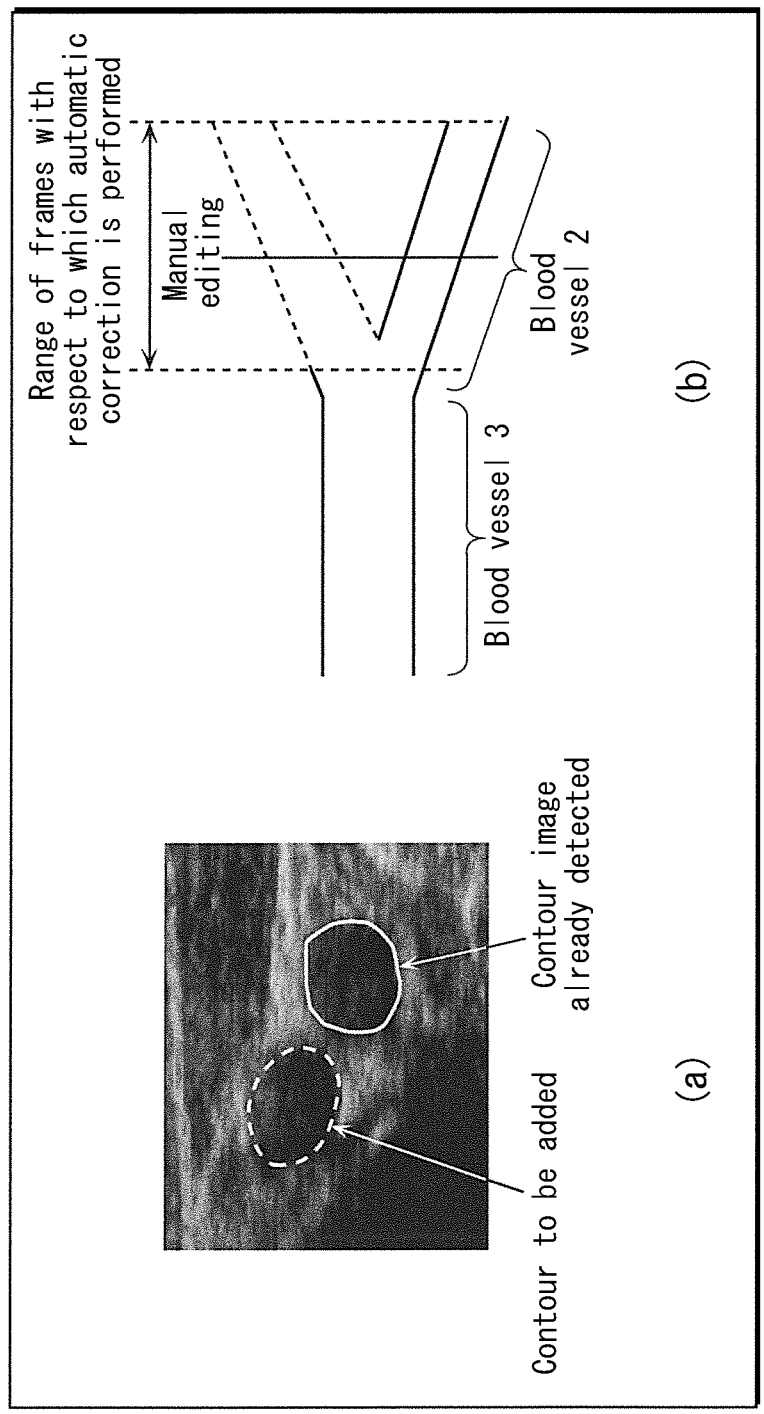
FIG. 16 is an explanatory diagram illustrating correction information and specification information related to the ultrasound diagnostic device pertaining to embodiment 3.

FIG. 16 is an explanatory diagram illustrating correction information and specification information received by the ultrasound diagnostic device 3 pertaining to the present embodiment. The specification unit 102A receives, from the user, correction information indicating, as a contour to be added to an ultrasound image, a contour of a blood vessel that has not been extracted from the ultrasound image by the contour extraction unit 101 (portion (a) of FIG. 16). In addition, the specification unit 102A receives, from the user, specification information that specifies a frame with respect to which manual correction of a blood vessel contour image is to be performed (a manual correction target ultrasounds image) (portion (b) of FIG. 16). Correction of a blood vessel contour image in the specified frame is performed in the same way as in embodiment 1 by using the correction information and the specification information.

Figure 17:
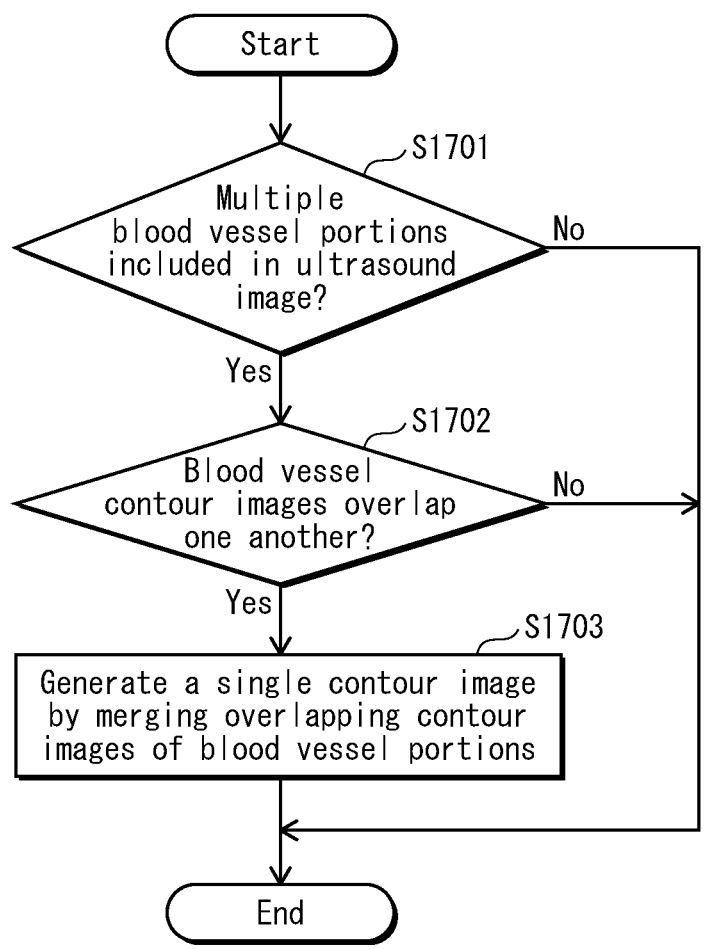
FIG. 17 is a flowchart illustrating merging processing pertaining to embodiment 3.

FIG. 17 is a flowchart illustrating merging processing pertaining to embodiment 3.

In Step S1701, the merging determination unit 101A determines whether or not a plurality of blood vessel contour images are included in an ultrasound image. Here, the plurality of blood vessel contour images may include a blood vessel contour image that has been added to the ultrasound image according to the correction information that the specification unit 102A has received from the user. When the merging determination unit 101A determines that the ultrasound image includes a plurality of blood vessel contour images, processing proceeds to Step S1702. Meanwhile, when the merging determination unit 101A determines that the ultrasound image does not include a plurality of blood vessel contour images, the merging processing is terminated.

In Step S1702, the merging determination unit 101A determines whether or not two or more contour images, among the plurality of blood vessel contour images in the ultrasound image, overlap one another. When the merging determination unit 101A determines that two or more of the contour images overlap one another, processing proceeds to Step S1703. When the merging determination unit 101A determines that none of the contour images overlap one another, the merging processing is terminated.

In Step S1703, the merging determination unit 101A generates a single contour image by merging the two or more overlapping blood vessel contour images in the ultrasound image.

Figure 18:
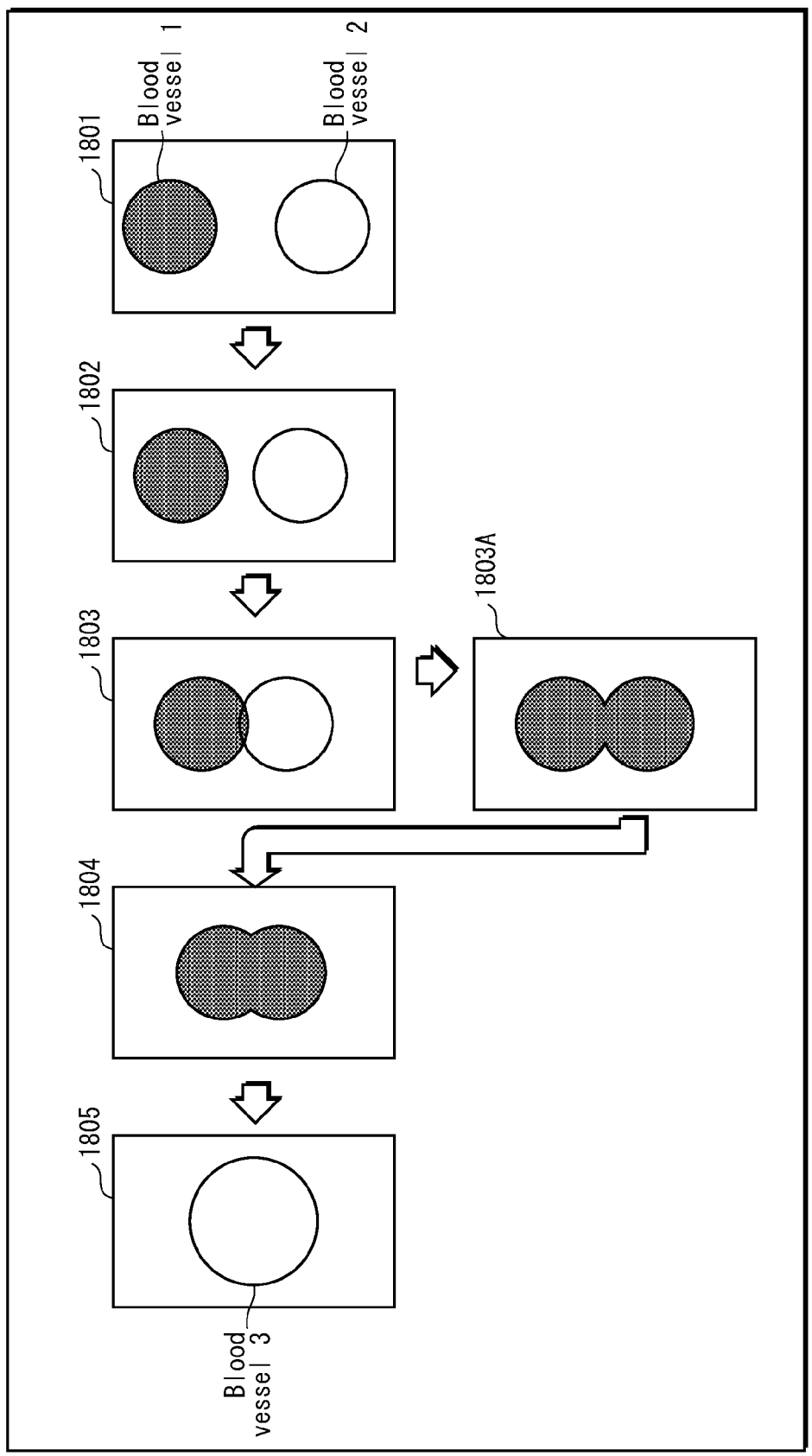
FIG. 18 is an explanatory diagram of the merging processing pertaining to embodiment 3.

FIG. 18 is an explanatory diagram of the merging processing pertaining to the present embodiment.

Frames 1801, 1802, 1803, 1803A, 1804, and 1805 illustrated in FIG. 18 are ultrasound images acquired from spatially-successive examination positions. Further, FIG. 18 provides schematic illustration of blood vessel contour images included in such frames. The ultrasound diagnostic device 3 performs contour correction starting from frame 1801 and proceeding to subsequent frames 1802, 1803, 1804, and 1805, in the stated order.

Frames 1801 and 1802 each include a contour image of the first blood vessel portion and a contour image of the second blood vessel portion. The first blood vessel portion and the second blood vessel portion correspond to those explained above with reference to portion (b) of FIG. 16, and are respectively indicated as blood vessel 1 and blood vessel 2 in FIG. 18. In each of frames 1801 and 1802, the contour images of the first blood vessel portion and the second blood vessel portion do not overlap one another. When the ultrasound diagnostic device 3 performs the merging processing as described above with respect to each of frames 1801 and 1802, a determination is made in Step S1702 that none of the contour images overlap one another, and thus, the merging processing is terminated.

Meanwhile, frame 1803 includes a contour image of the first blood vessel portion and a contour image of the second blood vessel portion, which overlap one another. When the ultrasound diagnostic device 3 performs the merging processing as described above with respect to frame 1803, the overlapping contour images of the first blood vessel portion and the second blood vessel portion are merged into a single contour image in Step S1703. In FIG. 18, the contour image so generated is illustrated in frame 1803A. Here, note that a determination may be made that two contour images are merged into a single contour image when a ratio of an overlapping area to a total area of a contour image exceeds a predetermined threshold value.

In frame 1804, contour images of the first blood vessel portion and the second blood vessel portion overlap one another with a greater overlapping area than in frame 1803. The ultrasound diagnostic device 3, already having generated the single contour image in frame 1803, performs a search in frame 1804 by using the single contour image in frame 1803A as an initial contour image and generates a blood vessel contour image.

Frame 1805 includes a contour image of the third blood vessel portion. The third blood vessel portion corresponds to that explained above with reference to portion (b) of FIG. 16, and is indicated as blood vessel 3 in FIG. 18. The ultrasound diagnostic device 3 performs a search in frame 1805 by using the single contour image in frame 1804 as an initial contour image and generates a blood vessel contour image in frame 1805.

As such, the ultrasound diagnostic device 3 generates a correct blood vessel contour image (correct blood vessel contour images) in each frame from frame 1801, which includes contour images of the first blood vessel portion and the second blood vessel portion, and up to frame 1805, which includes a single contour image of the third blood vessel portion.

Through application of the creation of a blood vessel contour image and the merging of blood vessel contour images as described above, a Y-shaped blood vessel can be extracted by using contour information specified by the user.

Figure 19:
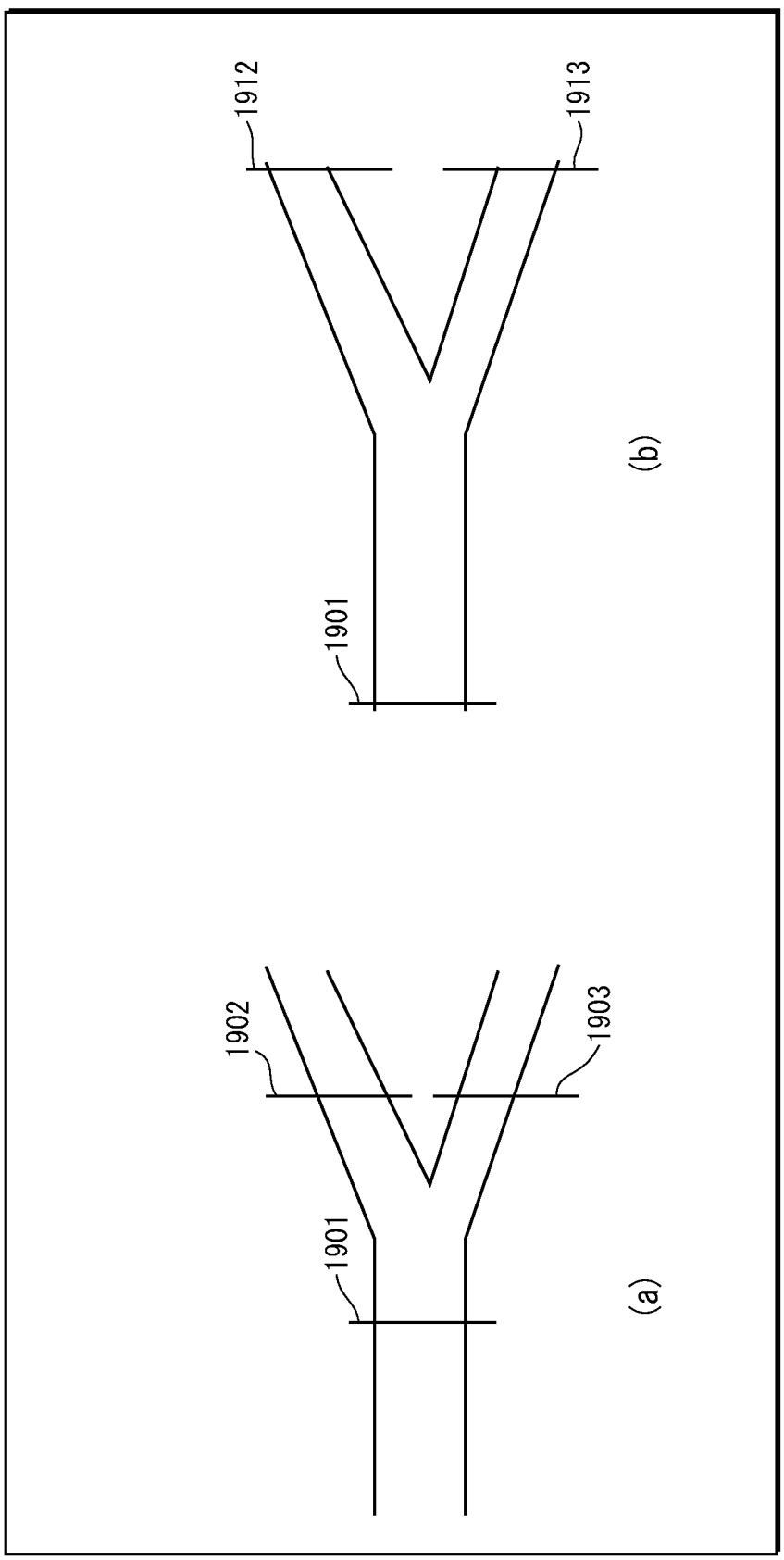
FIG. 19 is an explanatory diagram illustrating blood vessel extraction processing pertaining to embodiment 3.

FIG. 19 is an explanatory diagram illustrating blood vessel extraction pertaining to embodiment 3.

Portion (a) of FIG. 19 illustrates a case where an image of a contour of a Y-shaped blood vessel appearing in a plurality of ultrasound images is generated by using contour images generated from three blood vessel portions specified by the user. The user monitors the plurality of ultrasound images, and specifies contour images of the Y-shaped blood vessel at positions 1901, 1902, and 1903 of the Y-shaped blood vessel. Here, since an approximate position of an examination subject where a Y-shaped blood vessel exists is known, as is the case when examination subject is the human carotid artery, the user is able to acquire a plurality of ultrasound images including a branching part of a Y-shaped blood vessel.

The ultrasound diagnostic device 3 generates blood vessel contour images starting from each of positions 1901, 1902, and 1903, in both a positive direction and a negative direction with respect to the direction in which the blood vessel runs from each of positions 1901, 1902, and 1903. Note that when, for example, the generation of blood vessel contour images starting from each of positions 1901 and 1903 is first performed, and the generation of blood vessel contour images from position 1902 is subsequently performed, the merging processing is performed. Further, note that the closer each of positions 1901, 1902, and 1903 are set to the branching portion of the blood vessel, the more accurately the image of the contour of the Y-shaped blood vessel can be generated.

Portion (b) of FIG. 19 illustrates a case where an image of a contour of a Y-shaped blood vessel appearing in a plurality of ultrasound images is generated by using contour images generated from three blood vessel portions specified by the user from specific ultrasound images. Here, the specific ultrasound images refer to ultrasound images that correspond to end regions of the Y-shaped blood vessel in the direction in which the blood vessel runs. In this case, the generation of blood vessel contour images and the merging processing are performed in a similar manner as in the case illustrated in portion (a) of FIG. 19. According to the method illustrated in portion (b) of FIG. 19, the user does not need to make a specification of ultrasound images, and thus, the amount of labor on the side of the user is reduced.

As such, the ultrasound diagnostic device pertaining to the present embodiment enables newly creating, according to user specification, a blood vessel contour image that is not initially extracted by the ultrasound diagnostic device.

Further, when a blood vessel contour image newly created according to user specification overlaps with another blood vessel contour image, the ultrasound diagnostic device forms a blood vessel contour image by treating the two blood vessel contour images as a single blood vessel contour image.

Further, the ultrasound diagnostic device, when there exists a Y-shaped blood vessel a contour image of which is not extracted by the ultrasound image, newly creates a contour image of the Y-shaped blood vessel.

Embodiment 4

By recording, on a recording medium such as a flexible disk, a program for implementing the contour extraction methods described in the above embodiments, an independent computer system can easily execute processing described in the above embodiments.

Figure 26A:
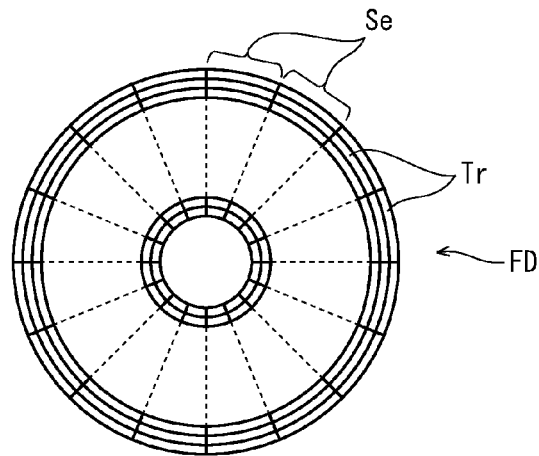
FIGS. 26A through 26C are explanatory diagrams illustrating a case where a contour extraction method is implemented on a computer system by using a program recorded on a recording medium such as a flexible disk.
Figure 26B:
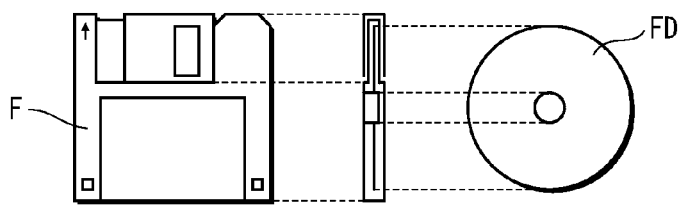
Figure 26C:
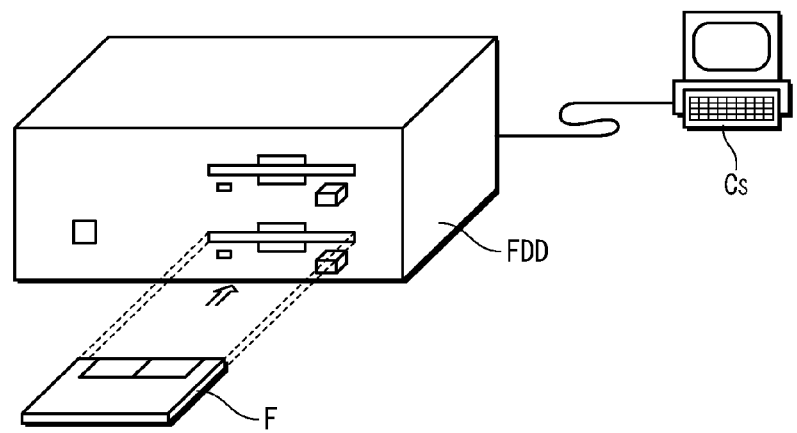

FIGS. 26A through 26C are explanatory diagrams illustrating a case where the contour extraction methods described in the above embodiments is executed by a computer system using a program recorded on a recording medium such as a flexible disk.

FIG. 26A includes: illustration of an exterior of a floppy disk when seen from a front side, illustration of a cross-sectional structure of the floppy disk, and illustration of an interior of the floppy disk (i.e., the flexible disk). FIG. 26A illustrates an example of a physical format of the flexible disk, which is the main body of a recording medium. The flexible disk FD is housed in a case F. A plurality of tracks Tr are formed on a surface of the flexible disk FD in concentric circles from an outer circumference to an inner circumference of the flexible disk FD. Each track is divided into 16 sectors Se in terms of angle from a center of the flexible disk FD. Therefore, a flexible disk having the above program recorded thereon has, in specific, the above program recorded on a region thereof allocated to the above program.

FIG. 26C illustrates a configuration for recording the program on the flexible disk FD and reproducing the program recorded on the flexible disk FD. When recording the program for implementing the contour extraction methods on the flexible disk FD, a computer system Cs writes the program to the flexible disk FD via a flexible disk drive. Furthermore, when constructing, in a computer system, the contour extraction control methods by using the program recorded on the flexible disk, the program is read from the flexible disk via the floppy disk drive and is transmitted to the computer system.

In the above explanation, explanation is provided while taking a flexible disk as an example of a recording medium. However, the contour extraction methods can be implemented by using an optical disc. Further, recording media usable for implementing the contour extraction methods are not limited to a flexible disk and an optical disc, and alternatively any media on which the program can be recorded, such as an IC (Integrated Circuit) card or a ROM cassette, can be used to implement the contour extraction methods.

Note that functional blocks of the ultrasound diagnostic device 1 illustrated in FIG. 1 are typically implemented by using LSIs, which is one type of an integrated circuit. The implementation of the above-described functional blocks by using LSIs may be performed such that a single LSI chip is used for each individual functional block. Alternatively, the above-described functional blocks may be implemented by using LSIs each including one or more of such functional blocks, or by using LSIs each including a part of each of the functional blocks.

Although referred to here as an LSI, depending on the degree of integration, the terms IC, system LSI, super LSI, or ultra LSI are also used.

In addition, the method for assembling integrated circuits is not limited to the above-described method utilizing LSIs, and a dedicated communication circuit or a general-purpose processor may be used. For example, a dedicated circuit for graphics processing, such as a graphic processing unit (GPU), may be used. A field programmable gate array (FPGA), which is programmable after the LSI is manufactured, or a reconfigurable processor, which allows for reconfiguration of the connection and setting of circuit cells inside the LSI, may alternatively be used.

Furthermore, if technology for forming integrated circuits that replaces LSI were to emerge, owing to advances in semiconductor technology or to another derivative technology, the integration of functional blocks may naturally be accomplished using such technology. The application of biotechnology or the like is possible.

Furthermore, the units of the ultrasound diagnostic device 1 illustrated in FIG. 1 may connect via a network such as the Internet or a local area network (LAN). For example, a configuration may be made such that ultrasound images are read from a server, an accumulation device, etc., located along the network and storing the ultrasound images. Further, a modification may be made such that the adding of functions to the units is performed via a network.

Figure 27:
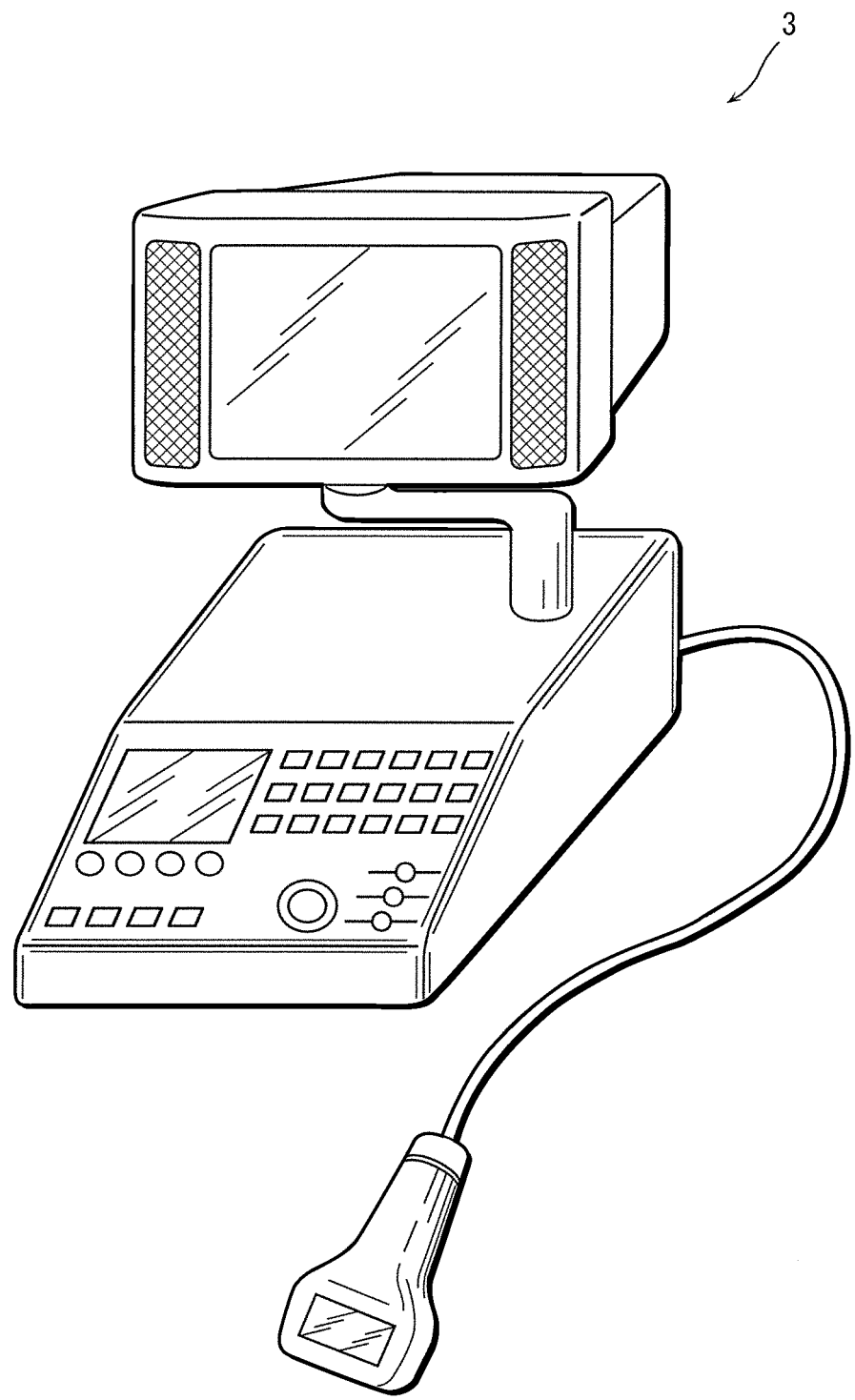
FIG. 27 illustrates an example of an ultrasound diagnostic device.

In addition, the ultrasound diagnostic devices in the embodiments may be implemented, for example, as the ultrasound diagnostic device 3 illustrated in FIG. 27.

INDUSTRIAL APPLICABILITY

The ultrasound diagnostic device and the contour extraction method pertaining to the present disclosure, when correction is to be performed with respect to contour images of a layer of a blood vessel extracted from a plurality of spatially-successive ultrasound images and a user manually corrects a contour image in one of the ultrasound images, automatically corrects contour images in neighboring ultrasound images according to the result of the manual correction. Thus, the amount of time required for the correction of blood vessel contour images is reduced by a great extent. Thus, the ultrasound diagnostic device and the contour extraction method pertaining to the present disclosure reduce time required for examinations, such as the examination for arteriosclerosis, in which the measurement of a thickness of the layer of the blood vessel is required. Accordingly, the ultrasound diagnostic device and the contour extraction method pertaining to the present disclosure are highly usable in the field of medical diagnostic devices.

REFERENCE SIGNS LIST 1, 2, 3, 1700, 2300 ultrasound diagnostic device
101, 1701, 2301 contour extraction unit
101A merging determination unit
102, 102A, 1702, 2302 specification unit
103, 103A, 1703, 2303 manual correction unit
104 target setting unit
105 correction information generation unit
106, 202, 1704, 2304 post-correction contour memory
107, 203, 1705, 2305 display unit
201 3D image generation unit
1101 B mode image
1102 magnified image
1103 slide bar
1104 frame

The invention claimed is:

1. An ultrasound diagnostic device comprising:
a contour extraction circuit configured to extract a first contour image from at least one of a plurality of ultrasound images obtained from spatially-successive examination positions and each including an image of a blood vessel, a contour image extracted from an ultrasound image being an image indicating a contour of the blood vessel and being extracted from an image of the blood vessel appearing in the ultrasound image;
a specification circuit configured to receive, from a user of the ultrasound diagnostic device, specification information specifying a manual correction target ultrasound image among the ultrasound images and correction information indicating details of a manual correction that the user performs with respect to a first contour image extracted from the manual correction target ultrasound image; and
a contour correction circuit configured to correct the first contour image extracted from the manual correction target ultrasound image according to the correction information to obtain a corrected first contour image in the manual correction target ultrasound image,
wherein:
the contour extraction circuit is further configured to (i) set, as a target ultrasound image, one of the ultrasound images that is obtained from an examination position adjacent to an examination position from which the manual correction target ultrasound image is obtained, (ii) set, with respect to the target ultrasound image, an initial contour image having a shape of the corrected first contour image in the manual correction target ultrasound image, (iii) perform a search with respect to the target ultrasound image by using the initial contour image set with respect to the target ultrasound image, and (iv) extract, from the target ultrasound image, a second contour image which is a contour image that is obtained as a result of performing the search with respect to the target ultrasound image.

2. The ultrasound diagnostic device of claim 1, wherein the contour extraction circuit extracts the contour image obtained as the result of performing the search with respect to the target ultrasound image as the second contour image only when the contour image obtained as the result of performing the search with respect to the target ultrasound image and a first contour image extracted from the target ultrasound image differ in shape by at least a predetermined level.

3. The ultrasound diagnostic device of claim 1, wherein:
the contour extraction circuit is further configured to (i) set, as another target ultrasound image, one of the ultrasound images that differs from the manual correction target ultrasound image and the target ultrasound image, (ii) set, with respect to said another target ultrasound image, an initial contour image having a shape of the second contour image extracted from the target ultrasound image, (iii) perform a search with respect to said another target ultrasound image by using the initial contour image set with respect to said another target ultrasound image, and (iv) extract, from said another target ultrasound image, a second contour image being a contour image that is obtained as a result of performing the search with respect to said another target ultrasound image.

4. The ultrasound diagnostic device of claim 3, wherein the target ultrasound image and said another target ultrasound image are obtained from adjacent examination positions.

5. The ultrasound diagnostic device of claim 4, wherein:
the contour extraction circuit performs multiple iterations of the search, each time processing a different one of the plurality of ultrasound images, the contour extraction circuit performing the search starting from the target ultrasound image, which is closest in terms of examination position to the manual correction target ultrasound image, and subsequently processing, one by one, other ones of the ultrasound images in order of closeness, in terms of examination position, to the manual correction target ultrasound image, and
when performing a given iteration of the search, the contour extraction circuit uses a contour image obtained as a result of performing a previous iteration of the search as an initial contour image.

6. The ultrasound diagnostic device of claim 5, wherein:
the contour extraction circuit performs said multiple iterations of the search while a contour image obtained as a result of performing a present iteration of the search and a first contour image extracted from one of the ultrasound images processed in the present iteration of the search differ in shape by at least the predetermined level.

7. The ultrasound diagnostic device of claim 1, wherein:
a contour image extracted by the contour extraction circuit from an ultrasound image indicates a contour of a tunica intima or a tunica adventitia of the blood vessel.

8. The ultrasound diagnostic device of claim 7, wherein:
the contour extraction circuit performs multiple iterations of the search, each time processing a different one of the plurality of ultrasound images, the contour extraction circuit performing the search starting from the target ultrasound image, which is closest in terms of examination position to the manual correction target ultrasound image, and subsequently processing, one by one, other ones of the ultrasound images in order of closeness, in terms of examination position, to the manual correction target ultrasound image, and
the contour extraction circuit performs said multiple iterations of the search while a distance between contour images of the tunica intima and the tunica adventitia, obtained as a result of performing a present iteration of the search, exceeds a predetermined threshold value.

9. The ultrasound diagnostic device of claim 1, further comprising:
a three-dimensional image generation circuit that generates a three-dimensional image of the blood vessel by combining contour images of the blood vessel extracted from the ultrasound images by the contour extraction circuit according to respective examination positions from which the ultrasound images are obtained.

10. The ultrasound diagnostic device of claim 1, wherein:
the specification circuit receives, from the user as the correction information, additional contour information indicating a contour image corresponding to another image of the blood vessel appearing in the manual correction target ultrasound image, and
the contour correction circuit corrects the manual correction target ultrasound image by creating the contour image corresponding to said another image of the blood vessel in the manual correction target ultrasound image.

11. The ultrasound diagnostic device of claim 10, wherein:
the contour extraction circuit is further configured to, when two or more contour images overlap one another in the manual correction target ultrasound image after the correction by the contour correction circuit, merge the two or more overlapping contour images into a single contour image, and extract the single contour image from the manual correction target ultrasound image.

12. The ultrasound diagnostic device of claim 10, wherein:
when (i) the specification information received by the specification circuit specifies, from among the ultrasound images, each of a first ultrasound image including one image of the blood vessel and a second ultrasound image including two images of the blood vessel as the manual correction target ultrasound image, and (ii) the correction information received by the specification circuit is additional contour information indicating one contour image corresponding to said one image of the blood vessel in the first ultrasound image and two contour images corresponding to said two images of the blood vessel in the second ultrasound image,
the contour correction circuit corrects the first ultrasound image by creating said one contour image according to the correction information and corrects the second ultrasound image by creating said two contour images according to the correction information.

13. A contour extraction method for an ultrasound diagnostic device, the contour extraction method comprising:
extracting a first contour image from at least one of a plurality of ultrasound images obtained from spatially-successive examination positions and each including an image of a blood vessel, a contour image extracted from an ultrasound image being an image indicating a contour of the blood vessel and being extracted from an image of the blood vessel appearing in the ultrasound image;
receiving, from a user of the ultrasound diagnostic device, specification information specifying a manual correction target ultrasound image among the ultrasound images and correction information indicating details of a manual correction that the user performs with respect to a first contour image extracted from the manual correction target ultrasound image;
correcting the first contour image extracted from the manual correction target ultrasound image according to the correction information to obtain a corrected first contour image in the manual correction target ultrasound image; and
(i) setting, as a target ultrasound image, one of the ultrasound images that is obtained from an examination position adjacent to an examination position from which the manual correction target ultrasound image is obtained, (ii) setting, with respect to the target ultrasound image, an initial contour image having a shape of the corrected first contour image in the manual correction target ultrasound image, (iii) performing a search with respect to the target ultrasound image by using the initial contour image set with respect to the target ultrasound image, and (iv) extracting, from the target ultrasound image, a second contour image which is a contour image that is obtained as a result of performing the search with respect to the target ultrasound image.

14. A non-transitory computer-readable recording medium having recorded thereon a program for causing a computer to execute the contour extraction method according to claim 13.

* * * * *